United States Patent
McDonnell et al.

(10) Patent No.: US 11,769,244 B2
(45) Date of Patent: Sep. 26, 2023

(54) SYSTEM, DEVICE, PROCESS AND METHOD OF MEASURING FOOD, FOOD CONSUMPTION AND FOOD WASTE

(71) Applicant: Orchard Holding, South Bend, IN (US)

(72) Inventors: Rian McDonnell, Chicago, IL (US); Elise Weimholt, Chicago, IL (US)

(73) Assignee: Orchard Holding, South Bend, IN (US)

( * ) Notice: Subject to any disclaimer, the term of this patent is extended or adjusted under 35 U.S.C. 154(b) by 0 days.

(21) Appl. No.: 17/670,477

(22) Filed: Feb. 13, 2022

(65) Prior Publication Data
US 2022/0270238 A1    Aug. 25, 2022

Related U.S. Application Data

(60) Provisional application No. 63/152,527, filed on Feb. 23, 2021.

(51) Int. Cl.
*G06T 7/00*    (2017.01)
*G06V 20/68*   (2022.01)
(Continued)

(52) U.S. Cl.
CPC ........... *G06T 7/0004* (2013.01); *G01N 33/02* (2013.01); *G06N 20/00* (2019.01); *G06V 10/141* (2022.01);
(Continued)

(58) Field of Classification Search
CPC .... G06V 20/68; G06V 10/10; G06V 40/1365; G06V 40/197; G06K 9/6267; G06T 2207/30128
See application file for complete search history.

(56) References Cited

U.S. PATENT DOCUMENTS

| | | | |
|---|---|---|---|
| 2006/0218057 A1* | 9/2006 | Fitzpatrick | G06Q 10/04 705/28 |
| 2013/0058566 A1* | 3/2013 | Sato | G06T 11/60 382/159 |

(Continued)

FOREIGN PATENT DOCUMENTS

KR    20190104980 A  *  9/2019

*Primary Examiner* — Guillermo M Rivera-Martinez
(74) *Attorney, Agent, or Firm* — Geeta Kadambi; RIDDHLIP LLC

(57) ABSTRACT

The system, device, process and method of measuring food, food consumption and waste with image recognition and sensor technology is presented to empower cafeterias, processors, quick service restaurants, and other institutions and locations to reduce food waste. Using kitchen and consumer data, the system allows food providers to characterize key food properties, optimize portion sizing, ingredient combinations, and meal preparation, to maximize profits and minimize excess. The current system, process and method optimize the food chain uses analytics and prediction insights. Gathering data through the use of a sensor package (typically including a camera system), and/or smartphone application, a digital platform is then used to give insights to institutions over time. This feedback includes food supplier changes, quality reports, preparation changes, portion sizing, ingredient usage, and customer feedback.

20 Claims, 25 Drawing Sheets

(51) Int. Cl.
*G06N 20/00* (2019.01)
*G01N 33/02* (2006.01)
*G06V 10/141* (2022.01)

(52) U.S. Cl.
CPC .... *G06V 20/68* (2022.01); *G06T 2207/30128* (2013.01)

(56) References Cited

U.S. PATENT DOCUMENTS

| | | | | |
|---|---|---|---|---|
| 2015/0206259 | A1* | 7/2015 | Takahashi | G06V 20/52 |
| | | | | 705/15 |
| 2016/0350514 | A1* | 12/2016 | Rajendran | G06Q 10/10 |
| 2017/0372240 | A1* | 12/2017 | Bender | G06Q 10/0633 |
| 2018/0018601 | A1* | 1/2018 | Wansink | G06Q 50/12 |
| 2019/0164116 | A1* | 5/2019 | Wallace | G06V 20/20 |
| 2022/0058388 | A1* | 2/2022 | Van Arnhem | G01G 19/52 |

* cited by examiner

SYSTEM, DEVICE, PROCESS AND METHOD OF MEASURING FOOD, FOOD CONSUMPTION AND FOOD WASTE

CROSS REFERENCE TO RELATED APPLICATION

This application claims priority to U.S. Provisional application 63/152,527 filed on Feb. 23, 2021. The contents of the said application is incorporated in its entirety herein by reference.

FIELD OF STUDY

This disclosure relates to a system, device, process and method of measuring, classifying, identifying and/or recording food, food consumption and food waste and to enable service providers, consumers, and other parties to assess food consumption and waste over a period of time.

BACKGROUND

Food production throughout the world is getting to a point where consumption is exceeding production. Population around the world is increasing. Food loss/waste happens because edible food is discarded at every point along the food chain: on farms and fishing boats, during processing and distribution, in retail stores, company cafeterias, institutes, healthcare facilities, fast food chains, in restaurants, cafes and at home.

Additionally, in 2015, the USDA and the US Environmental Protection Agency adopted federal targets to cut food waste by 50 percent by 2030. In 2016 a survey by the Ad Council of 6700 adults, 75 percent of respondents said that food waste was important or very important to them. However, limited data makes it difficult to assess whether this awareness has turned into action and whether or not people are actually wasting less food now than they were before. Homes remain a large source of food waste and more needs to be done to help educate the public and provide people with resources to help them implement food saving practices at home.

Another reason why food waste has become such a large problem is that it has not been effectively measured or studied. A comprehensive report on food losses in the US is needed to characterize and quantify the problem, identify opportunities and establish benchmarks against which progress can be measured. Current commercial solutions for systems of measuring food wastage utilize manual food logging methods. The kitchen staff place food waste in a waste receptacle, and then manually confirms the weight and food type on a display connected to a waste receptacle. Due to the human input required of these systems, they are not deployed in customer facing applications, and are scarcely used in kitchens and production lines. Customers are not willing to manually enter food consumption data, they just want to throw their food away after eating a meal in a cafeteria setting. There is an urgent need to solve this issue with technology.

SUMMARY

This disclosure elaborates on the system, device, process and method of measuring food consumption and food wastage. The current state of the art for commercial food detection relies on manual entry. The instant system, device, method and process system automates food detection on multiple foods at once, both before and after meals (i.e., initial meals and plate scraps). In one embodiment, a system for measuring the incoming food, consumption of food and wastage of food is disclosed. In another embodiment, the wastage of food for the individual consumer is measured using purchased food data, and measurement of food in the waste disposal. In another embodiment, restaurant food wastage can be measured by inventory calculation, preparation area image capturing, associated waste disposal in preparation, food plate imaging of food served, food plate imaging of food after consumption, and/or food thrown away in garbage calculation. In one system, a cafeteria food consumption, sale and wastage can be analyzed by inventory, display unit volume, plate volume and then garbage disposed food volume. In one system, a food production line, procurement, processing, sale and wastage can be analyzed by inventory, display unit volume, package volume and then disposed food and unprocessed food volume.

In one embodiment, the system not only gathers but also analyses, calculates, predicts, and prevents wastage. In one embodiment, the method of measuring food consumption and wastage is customized based on user profile. In one embodiment, detection of food object property(s) is done prior to use, analysis of property(s) is collected as base data, aggregate time-based data is used for calculation and prediction using artificial intelligence engine applied through analytical module that would enable the generation of insights and trends from data which could further be shared with user/clients/enterprise etc.

In one embodiment, a process and system encompasses a specific device to capture food production, consumption and wastage, a database to record, store and isolate client data, a computer or a processor to capture, analyze, calculate, predict and display pertinent data through a user interface on a computer or other device for a client. In another embodiment, a process may cover the requirement in one location or multiple locations simultaneously.

In one embodiment, a software architecture for the entire software application to run locally after being downloaded on a computer, with only uploading back-up data to the cloud as disclosed. The benefit of this configuration is that a user can interact directly with the data that the devices (e.g. cameras) are capturing through the software user interface are disclosed. In one embodiment, a specific user based access is provided to a specific user to access specific data, wherein user is one of a manager, user, a quality control user with access to specific view of a real time data, data overview, data context and quality control view based on providing a specific access.

BRIEF DESCRIPTION OF DRAWINGS

Example embodiments are illustrated by way of example only and not limitation, with reference to the figures of the accompanying drawings, in which like references indicate similar elements and in which.

Figure 1:
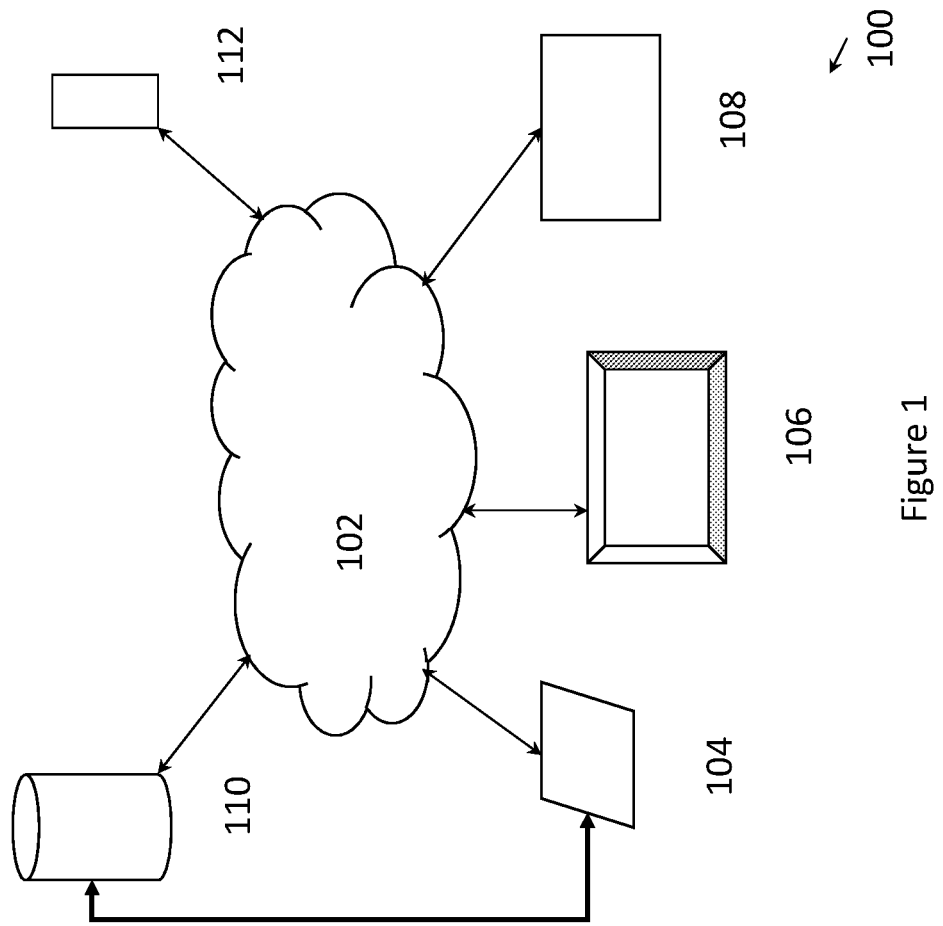
FIG. 1 is a view of the high level system dependencies for the current system, device, process and method.

Other features of the present disclosure will be apparent from the accompanying drawings and from the detailed description of embodiments that follows.

DETAILED DESCRIPTION

The instant disclosure describes a system, device, method and process to capture food, amount of incoming food, consumption of food and wastage of food in an individual or multiuser scenario or in a commercial or household domestic scenario. Increase in current population and climate change mandates us to access food loss and wastage so that the food starvation does not become a pandemic. The instant system, device, method and process lends itself to address this issue. Measuring is one of a calculating mass, weight, volume, dimensional analysis, composition, morphology, etc., for food. Food can be defined as any edible or consumable substance, including: human edible food, pet food, animal feed, energy crops, etc. Food consumption can be steps at several stages such as, but not limited to, intake, preparation, trimming, processing, storage, butchery, storage, maturation, shipping/transport, slicing, etc. The food processing and consumption may end not only at garbage disposal but also may be measured after butchering, mincing, dicing, packing, slicing, cooking, washing, blanching, marinating, coating stages.

Device hardware design is as follows: The specific device (FloWaste) is designed to capture relevant food data, while being protected from ingress and the environment. A custom designed, enclosure is used to hold any one, or a multitude, of sensors along with a processor to manage these sensors and data communication functions, a set of LED light indicators, and/or a LED scene illuminator optionally. The internal electronics are capable of housing a variety of sensors including; visual camera, stereo camera, NIR (Near-infrared) sensor and emitter, other hyperspectral sensors, laser scanners, LIDAR, radar, ultrasound sensors, optical projector, and more. The internal electronics are also capable of being connected to external sources such as a load cell, human machine interface, robotic operators, motors, lighting systems, etc.

The electronics assembly (sensors, processor, holder, LED indicator lights, LED scene illuminator, etc.) is enclosed within the ingress protection housing. This housing protects the electronics assembly from water, dust, static, earthing, or other external factors. This housing consists of 7 distinct parts, and 4 screws.

Transparent polymer/glass covering
Rubber/polymer seal
Transparent or opaque polymer/metal covering
Cable grommet plastic casing
Cable grommet rubber O-ring
Cable grommet plastic circular fastener
Cable grommet plastic nut When assembled, the sensors "transmit/operate/scan" through the transparent covering to gather the relevant food data. The rubber/polymer seal is attached between the transparent covering and the opaque covering, for the entire circumference, to ensure no ingress is possible. The opaque covering protects all components within and is a mounting point through 4 screws for the transparent covering. The opaque covering is also more ductile material to customize and manufacture with.

The cable grommet assembly is made up of the 4 cable grommet components (plastic casing, O-ring, plastic nut) and is attached to the opaque housing to allow electrical power to be passed into the housing, without sacrificing the ingress protection qualities of the housing. The cable grommet assembly does this by attaching to a drilled hole in the opaque casing, and can be fastened tight using the plastic nut to achieve sufficient sealing pressure. A small rubber seal around the outside of the cable grommet plastic casing ensures the outer diameter is sealed. The power cable passes through the internal diameter of the cable grommet assembly, where the rubber O-ring is present. The plastic circular fastener can be tightened to ensure the rubber O-ring forms a tight seal around the power cable.

A series of nuts and bolts are used to attach the opaque enclosure to the positioning arm. The positioning arm is a component that is designed to position the sensor at a desired location so it can collect the relevant food data. The specifications of this arm can vary depending on customer requirements. This arm can be mounted to the ceiling, wall, a work surface, a trash bin, a floor, or any other relevant surface or object. This mounting is typically accomplished using a clamp mechanism or permanent fasteners. All hardware components are either purchased "off-the-shelf" or manufactured. Manufactured parts consist of:

Electronics holder: Designed to hold sensors, processor(s), LED indicator lights, LED scene illuminator(s), and any other relevant electronics. This component is highly customized and novel to accommodate all relevant electronics. May be 3D printed but not exclusively 3D printed.

HSF protector (if needed for the technology): This piece is designed to protect the flexi cable, sometimes known as "HSF signal cable" between the sensor and processor. Adhesive is used to secure it around the cable and attached to the cable, camera and vision processor.

Stereo Camera Assembly (e.g. Intel Real Sense stereo camera sensor is installed): If Intel Real Sense cameras are used, the stereo camera assembly is created using the Intel camera module, Intel vision processor, HSF cable (of defined length), HSF protector, and adhesive. This assembly creates 1 distinct camera unit that can be attached to the complete assembly within the electronics holder.

LED light indicators: The LED light indicator assembly is manufactured using colored LEDs (red, white, and green typically), connecting wires, butt splice (or similar) crimp connectors of 2 different sizes. Each LED has a power and ground. Typically 2 LEDs of each color are used, so 6 total. The 6 ground wires are wrapped together and crimped into 1 large butt splice, which is then crimped to a single ground wire that carries the signal to the processor. Each set of colored LEDs is crimped together in a small butt splice (e.g. 2 red LEDs), which is crimped to a single wire that carries the power signal from the processor.

Printed Circuit Board (if custom PCB is used as processor): If a custom FloWaste PCB is being used as a processor, this is manufactured using standard PCB printing, and etching process for a multilayer PCB.

Ingress Protection housing: The ingress protection housing is altered to allow power cable to enter and provide power to the processor (or power distribution board). The ingress protection housing can also be edited for additional cables to pass in or out for a variety of purposes, e.g. wired communication link, send data to end effectors/equipment, receive or send data to a human machine interface (HMI), receive data from external sensors, or send data or power to external sensors. This is done, while maintaining ingress protection, using a cable grommet. A hole is drilled into the opaque covering. The cable grommet assembly attaches and seals this hole, while also sealing around the cable that passes through its inner passage.

Power cable: A standard power cable (5-230 W, typically 15 W) is inserted into the cable grommet during assembly. The power cable sometimes needs to be resealed with the ground and power wires reconnected if it has been cut for insertion, and then the insulation layer sealed using heat shrink. A section of the cable is also reinforced with tape or similar material to increase the thickness and ensure a tight seal in the cable grommet.

Positioning Arm: The positioning arm is used to place the relevant sensors, within their housing/covering, in the desired location. Therefore the positioning arm is attached to the housing and a mounting point which could be the floor, a table or workstation, the ceiling, a trash bin, or similar surfaces and objects. The positioning arm is typically plastic, aluminum, or stainless steel, depending on the application. Arms can be customized using CNC milling, to change surface finishes, thickness, angles, lengths, widths, and bolt holes. Typically the arm is extruded by a $3^{rd}$ party before purchase, then FloWaste CNC mills both ends of the arm to meet the install specifications. Currently 2 or 4 bolts and nuts are used to attach the ingress protection housing to the mounting arm, through 2 or 4 drilled holes. When the 2 or 4 nuts and bolts are tightened in position, a liquid rubber/polymer/elastomer sealant is sprayed within the ingress protection housing to ensure the area is sealed and protecting against ingress. The other end of the positioning arm is typically attached to a mounting point with a clamp or with 4 bolts and nuts drilled into a surface.

Clamp (if custom clamp is used as mounting point): If a clamp is being used to mount the positioning arm, and therefore the entire assembly, a number of clamping positions are available. This clamp device typically clamps to a surface (table or workstation, the ceiling, a trash bin, or similar surfaces and objects) with 1 clamping mechanism, while a 2nd clamping mechanism, or a different attachment mechanism, is attached to the positioning arm. Clamp can be articulated and rotatable so that the sensor can be moved in X, Y, and Z planes as needed.

An example of an assembling the hardware device is described below: Stereo Camera Assembly (or other similar sensor assembly): Attach HSF cable to a stereo camera. Slot HSF Protector into gap between HSF cable and Real Sense module fully. The HSF cable should be covered by the HSF protector on 3 sides. Attach the Real Sense Vision processor to the HSF cable, ensuring the pins have completely clicked into place. Use adhesive to secure the assembly together on the exposed side of the HSF cable. Inject adhesive at both ends of the cable, where the camera and vision processor are attached. The entire assembly should be held on a flat surface until adhesive cures. Attach the cable (USB-C) to the vision processor and use adhesive to secure this connection.

Electronics Holder: The sensor assembly slots into the electronics holder with a light press fit. The sensor assembly can then be sealed to the electronics holder using adhesive in specified locations chosen to ensure thermal conductivity is not affected. Repeat steps above for any other sensors or electronic components needed. Mount the processor to the electronics holder at the specified mounting points. This is typically done with screws, but can also use adhesive. Connect the relevant sensors and other electronic components to the processor, and secure these connections with adhesive were required.

Transparent Covering: The Electronics Holder is designed to be a press fit within the transparent covering piece of the ingress protection housing. Pushing the Electronics Housing completely into the transparent covering results in this press fit. Adhesive can be used to ensure the electronics holder is held in this position during transport or similar scenarios. Fit the rubber/polymer seal into the groove along the circumference of the Transparent Covering.

Opaque Covering: Install the Cable Grommet and power cable as outlined previously in the manufacturing section. Attach the mounting arm to the Opaque Covering as outlined previously in the manufacturing section, ensuring ingress protection.

Ingress Protection Housing: Using 4 screws, attach the Transparent Covering to the Opaque Covering and ensure a sealed interface.

Mounting Arm: The mounting arm has been attached at one end to the Opaque Covering above. The other end should be attached to the mounting mechanism for the application, typically a clamping solution, or nuts and bolts.

Clamp: If a clamp is in use, it should be assembled with the relevant screws, nuts, bolts, and other fasteners. Attach the clamp to the mounting surface and the mounting arm.

FIG. 1 is a block diagram of an example of a food, food consumption and waste measurement management system 100, according to one or more embodiments. Particularly, the system is supported by server 104, imaging devices 106, 104, 108, and 112, which may be mobile devices image scanning devices or installed image device for collecting data, images, streaming videos and performing analytics, a network 102, a database 110. A network 102 may be one of a cloud services, local area network (LAN), wide area network (WAN), metropolitan area network (MAN), extranet, intranet, internet, peer-to-peer network, ethernet, or the like or a combination thereof. In the case of a wireless network, may comprise, but need not be limited to HomeRF, HiperLAN, Bluetooth, Zigbee, WiMAX, Wibree, FM, AM, 802.11 (G, N), WiFi and satellite, Wireless ISP, Satellite Broadband, Mobile Broadband, Local Multipoint Distribution Service and satellite communication systems etc. In one embodiment, the system may be a server-client system with processing occurring on one or more computers or other mobile/fixed devices connected through a network 102. In another embodiment, the system may be a peer-to-peer system with processing occurring in all computers or mobile devices connected through a network 102. In one embodiment, data is aggregated and stored in a central database server 110 connected to one or more computers or servers either directly or through a network 102. In another embodiment, data stores may be distributed among various devices and servers in the system.

Figure 2:
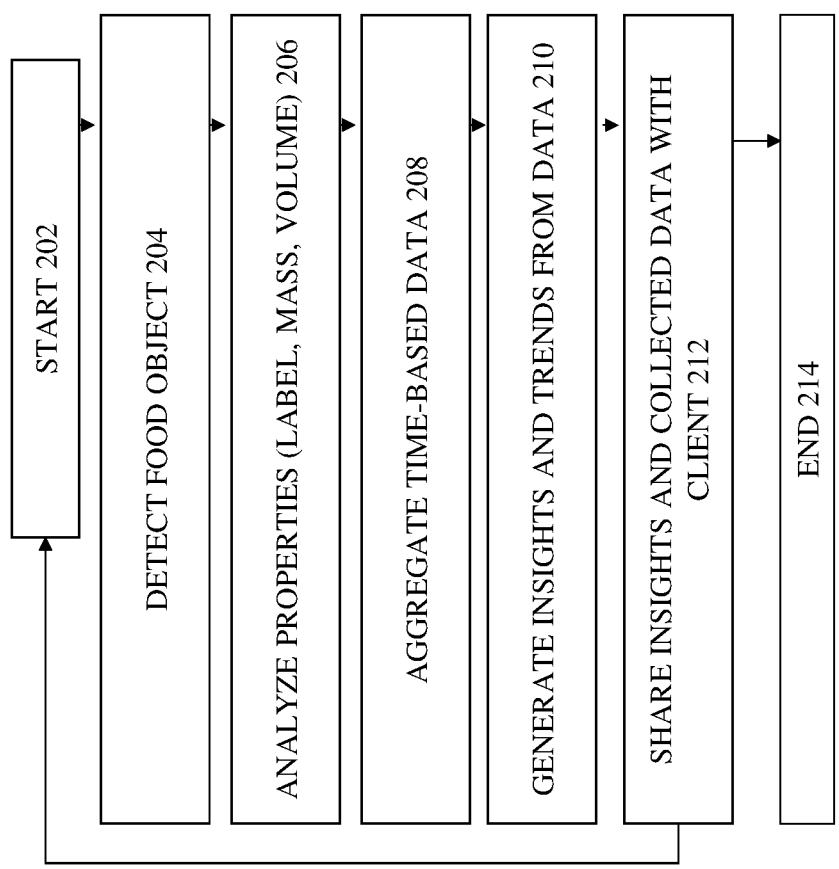
FIG. 2 shows a flow chart of detecting food objects.

FIG. 2 shows the food, food consumption and waste measurement management system is capable of detecting food objects. The method of performing the calculation, prediction and reporting of food consumption and wastage is described in a flow chart on FIG. 2. FIG. 2 shows a start 202 of the process and method by detecting food objects. The detection process may be automated or manual. The device uses cameras, infrared devices, image capturing devices, 3D image capturing, QR code readers, and/or grocery buying patterns, or order delivery suppliers, and scanning by users. When a food object is detected 204 the food, food consumption and waste measurement management system can analyze the food to calculate key properties. Including identifying the food category/type, mass of the object, volume, color, composition, quality, attributes, etc., 206. These individual instances of food detection can be aggregated over time 208. This aggregated data can then be used to generate insights and trends 210 instantly or for analysis later. These generated insights and trends can be shared with the client, along with any other collected data 212. The food consumption and waste measurement management system can iterate and repeat, or be terminated 214. The analysis step may use labels for food types, mass and volume of the food item. The step that follows is critical for aggregating time based data and may be repeat reading for the same time frame. The generation of insights for food quality, presentation to agreed standards, food procurement, food preparation, consumption/usage trend, wastage trend while prepping, per plate food distribution, per plate food consumption, per plate wastage, shelf life dependent wastage, consumption wastage, and popular food vs un popular food on the menu, more trendy food items, nutritional and calorific value that was consumed for personal use, seasonal inflow of perishables vs wastage etc., can be calculated using stored and immediate data gathering using cloud storage and processing algorithms. The process of sharing insights with clients for them to change their quality standards, financials and stop food wastage can be done using customized graphical user interface. In addition, real time image/video streaming allows users to measure performance remotely and continually from any worldwide location creating a massive improvement on management effectiveness. An API or other method can be used to integrate data into existing solutions, and notifications via SMS, email, other messaging, push notifications, etc.

Figure 3:
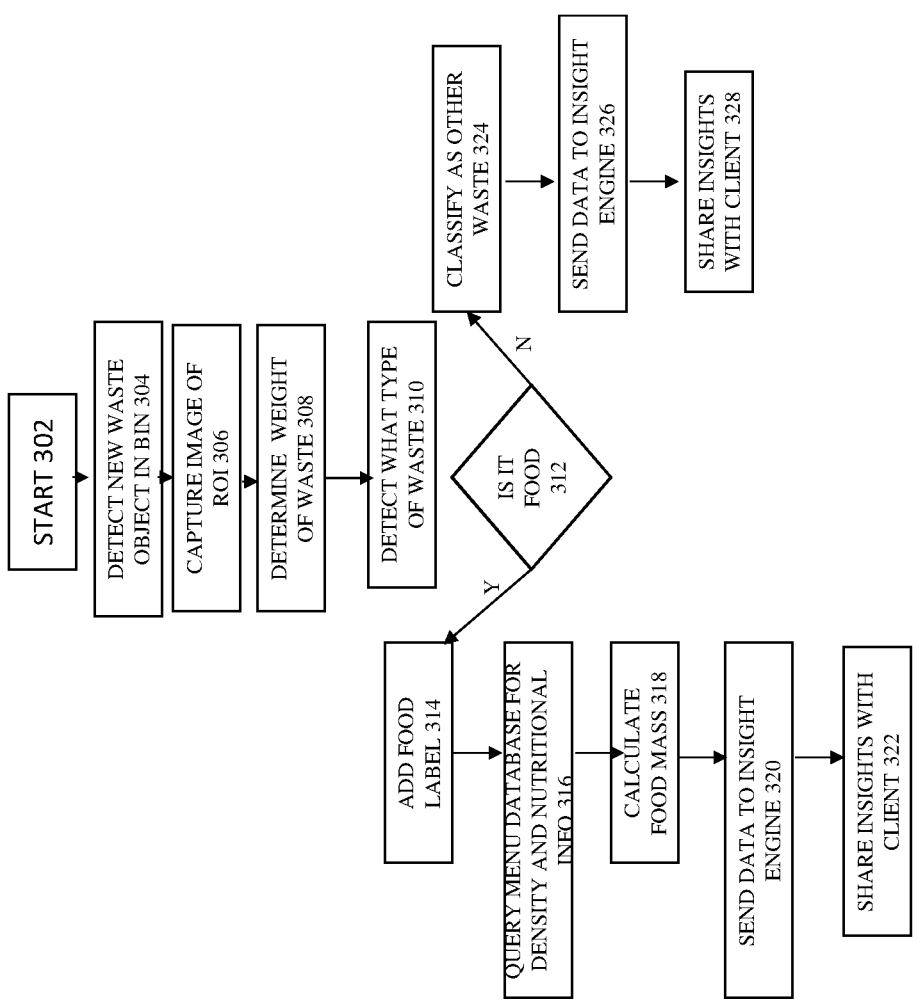
FIG. 3 shows a flow chart of process and method for food consumption and waste.

FIG. 3 shows the flowchart for the food characterization, food consumption and waste measurement management system, in one embodiment, is initialized with a start sequence 302. When a new object enters the region of interest (e.g. trash bin), the sensor or sensors detect the object 304 and capture the relevant data 306 (e.g. an image, video, series of images, point cloud, etc.). After this data is captured it can be used to determine key characteristics of the object, such as weight/mass/quality 308. The object can also be classified/identified 310 further. With the data presented, the system decides if the object is a type of food, or not food 312. If it is determined that the object is not food, it is classified as other waste 324. This data is then sent to the insight engine and used in key insights and/or trends 326. These insights and trends can then be shared with the client 328.

If the object is recognized as food then the image analysis module will add a label (314). After labelling query the database for nutritional requirement or direct spectroscopic measurement and density for the said food object (316). Calculation of the food mass (318) is performed and the data is sent to insight engine (320). The client then gets a chance to see or the analyst will share the results with client (322).

FIG. 3 shows flow chart of process for categorizing food waste using the camera sensor data collection method. A camera is installed above a waste receptacle, and detects when a new waste object enters the bin through a volume change trigger. The Region of Interest (ROI) of the object is captured in an RGB Image, which is the input into the machine learning object detection model. This detection model outputs whether the waste is food, or some other waste, like packaging. If it is classified as other waste, the volume is logged to the insight engine, but no further analysis is completed. If the object is classified as food waste, it is then sent to a second object detection model. In one embodiment, where we do analysis on non-food objects. In one embodiment one can identify if it is plastic, paper etc. and other key features e.g. recyclability, how compostable it is, etc. This model, in conjunction with menu data when possible, outputs a food label, along with a reference to the food label database, which includes information like density and nutritional breakdown. The weight of the object is determined from the stereo vision sensors, load cells, etc., which compute the volume. The weight is then estimated by multiplying the volume and the density of the identified food. The resulting data is sent to the insight engine, which is cloud hosted. On the cloud, the data is aggregated and analyzed for trends. From these trends, insights are generated and shared for the client to improve their food operations. The reason for two models is to allow a higher fidelity of the food trained model to be able to detect within numerous different food classes.

Figure 4:
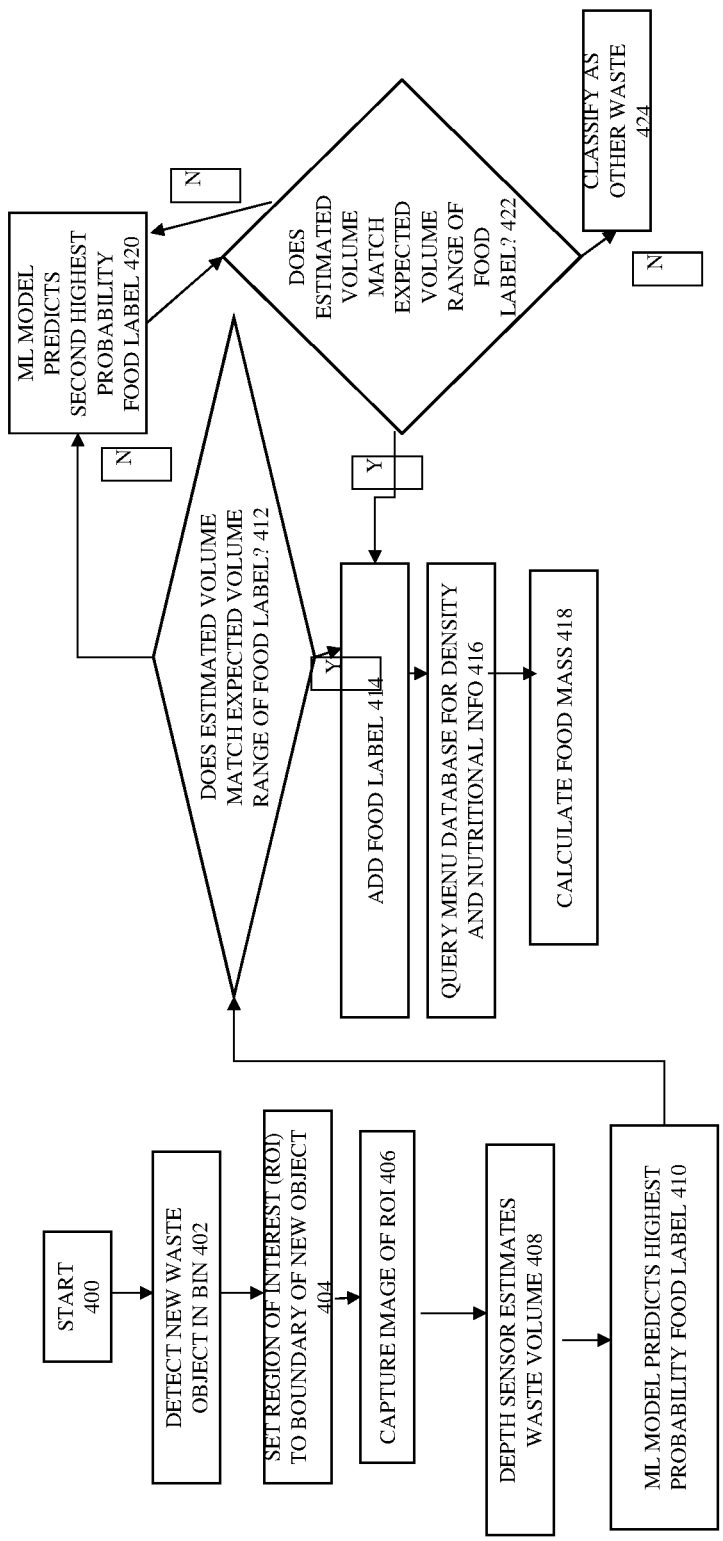
FIG. 4 shows calculation process of food waste.

FIG. 4 shows the flowchart for the food consumption and waste measurement management system, in one embodiment, is initialized with a start sequence 400. When a new food object enters the area of detection, the sensors detect the object(s) 402. The food object region of interest can be set around the boundary of the detected object(s) 404, and the relevant data can be captured (e.g. an image) 406. A depth sensor can be used to estimate the volume of the object(s) 408. The machine learning model predicts the highest probability food that matches with the object, using a single data source or variety of data sources 410. The system performs a check on the volumetric calculation to assess if it is within the expected range for the food type in question based on plate menu standards or other data points 412. If it is outside of the expected range, the next most probable food label is selected 420. Once again, the volume is assessed to see if it is within the expected range for the food type 422. If it is not, the process repeats until a threshold low probability is reached, at which point the object is classified as other waste 424. If the volume does fall within the range, the food label is assigned to the new food object 414. The menu data from the database can be queried to find the density and nutritional information associated with the food object 416. The mass of the food object can be calculated using the density and volume 418.

Figure 5:
FIG. 5 shows a garbage can with organic and non-organic trash in it.

FIG. 4 shows a similar flow chart process to that of FIG. 3, but after the waste has been classified as food. This process checks the computed weight of the object against the expected weight, and determines if there is a true match. If there is not, then the second highest probability food label that the food recognition model returned is used, and the process repeats. If the model is unable to accurately confirm a food label and volume profile, then the food object is classified as other waste. FIG. 5 shows a garbage bin 502 to be imaged for the food consumption and waste measurement management system to calculate the waste. Given an image or a video (treated as continuous series of images), we wish to identify certain items in it with bounding boxes or with other segmentation of the area (e.g. polygons, or semantic segmentation of pixels). For example, given a picture of a trash can, identify what food object components are in it to calculate the type and amount of food wasted. This pertains to a food object detection problem.

Figure 6:
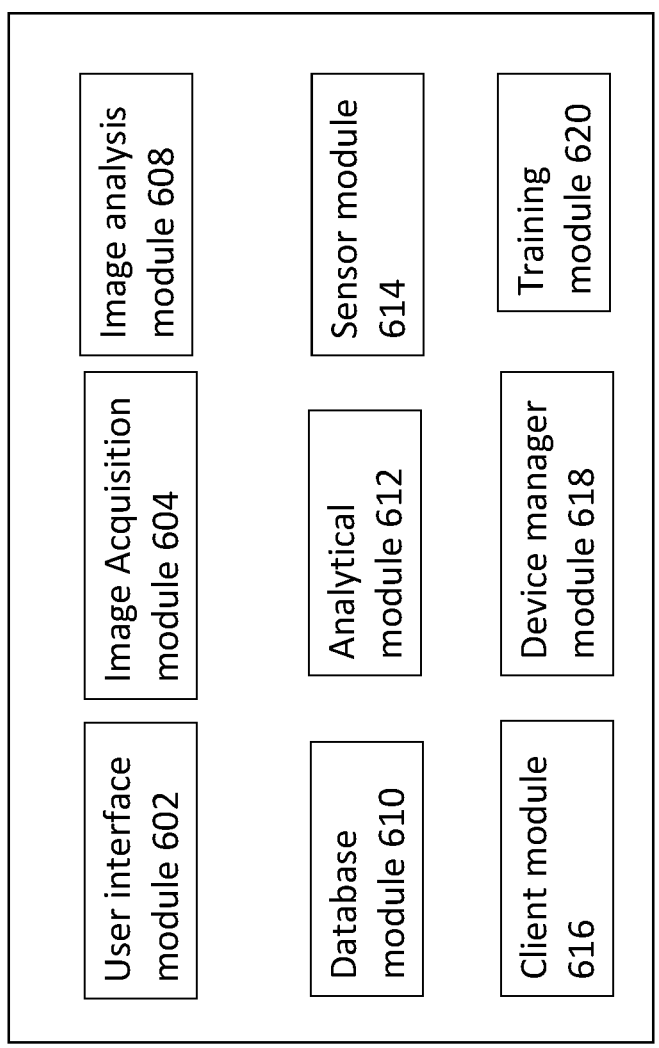
FIG. 6 shows Analytics modules in one embodiment.

FIG. 6 shows the food, food consumption and waste measurement management analytics (600) for captured video/image stream analytics. The user interface module 602 is installed on a user device or analytical person device to operate the device and process data either in-house or remotely. The user interface module capabilities depend on the software version customer choice. A user interface module (602) is installed at the user site, provided as a connecting portal to clients/user using network, or directly on the cloud based platform for installing, use, data gathering and data visualization functions.

The image acquisition module 604 connects the sensor and the image gathering device in use for capturing images such as, but not limited to, static images, live images, streaming images, video, spectroscopic images, etc., and the output from these single unit or multiple unit device images are stored in databases for analysis by image analysis module, used by training module to train datasets for analytical module, An image analysis module (608) collects data from sensor module, database module and training module to performs any preprocessing of data and image acquired using sensors situated in image acquiring devices and processes the data to be provided to the user, client or an analyst. Analyst may advise client or user for optimizing food acquisition based on food wastage data. An entity such as a company, restaurant or any other single user or multi user organizations may use this data to stream line buying, training employees, advising entities to serve what is being used, nutritionist to calculate what changes need to be made for providing balanced diet etc. The graphical user interface allows the user or the consultant who sets up the system for the client to choose the settings for a given case. The user can have access to controlling the sensor module, image acquisition module using the client module 616. The client module 616 is customizable for all access or limited access based on licensing requirements. Even at a single user facility the device manager module 618, training module 620, database module 610 and image acquisition module 604 may be limited to experts and other users restriction can be improved from user interface module 602. Data analysts may have access to training module 620, analytical module 612, database module 610 and image analysis module 608 for performing data analysis function.

The multi device sites and single device sites may have different requirements. Cloud based infrastructure benefits all users, either single or multiusers. As a process the network switch appliance with its system performs an entity detection module to pass frames from one or more streams through a training module 620 on a conventional processing hardware to obtain regions of interest in the frames; an entity alignment module to process regions of interest obtained from an image detection module, sensors module 614 located on the device and apply any differentiating factors between organic vs non organic matter, plastic vs edible matters, food initially served or taken by the person and what was thrown away in the garbage bin. All this data is analyzed using analytical module 612. The client module 616 enables service providers to set up the client case according to their requirements for access, data analysis, database storage etc.

The training module 620 uses data from process flow chart of FIG. 4, FIG. 3, FIGS. 14-16 for collection of data, stores it in database and provides input to the analytical module 612. Image analysis module 608 enables image analysis of captured images from a device when a person picks up the tray full of food, either by weight or by weight and image capture and when the tray is returned or by real time image analysis (motion detection, volume thresholding, etc.). The same insight engine that hosts the image analysis module and cloud hosted analytical module for food waste insights and feedback. Meal nutrition information, for example in a school cafeteria can be done using this system. Children's parents can be given feedback on their nutritional status as can the individual user. Nutrition specialist at hospitals, or any other work place can determine the patients or any subject's nutrition breakdown and eating habits.

Figure 7:
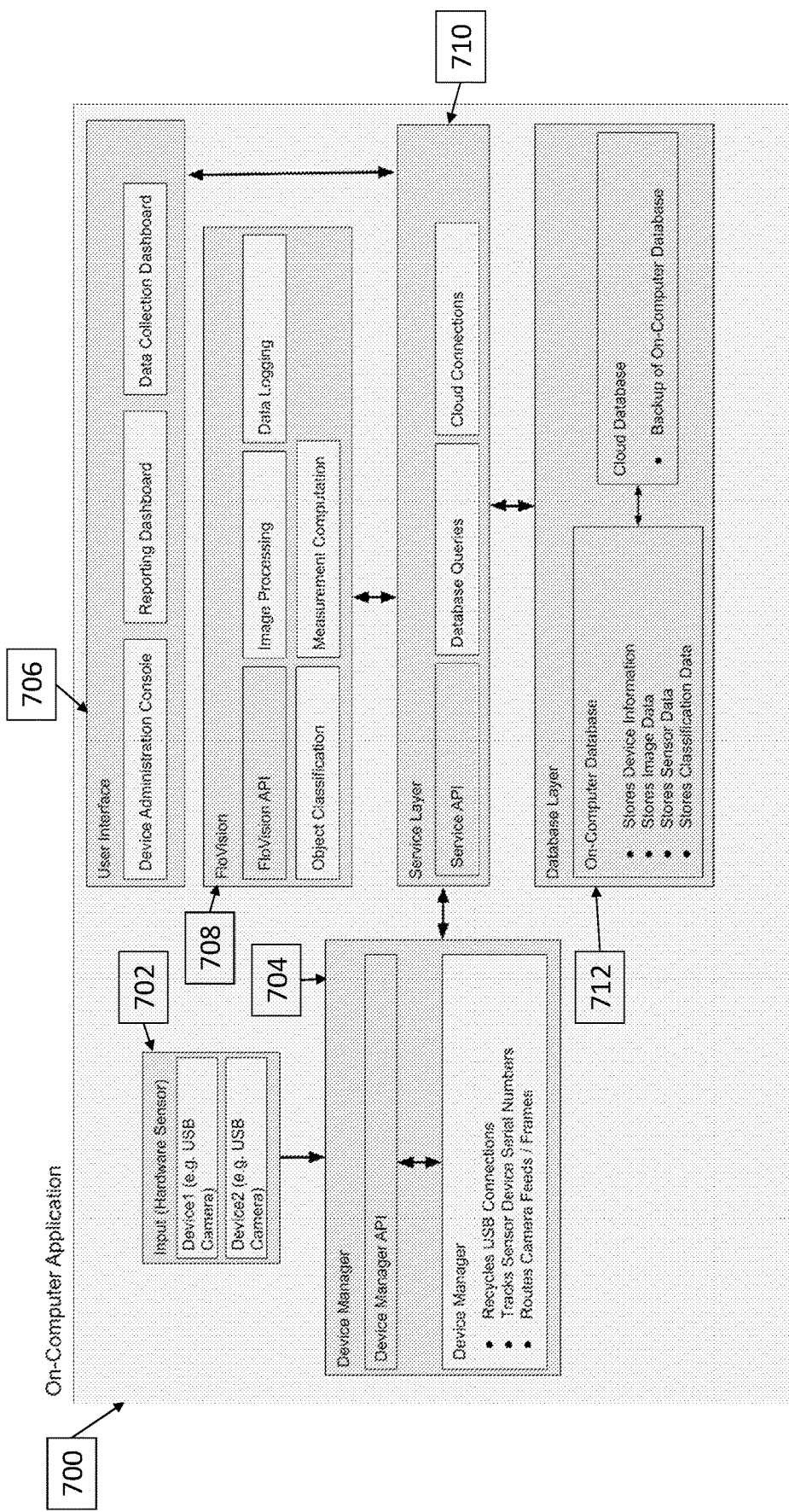
FIG. 7 shows on computer application of the food consumption and waste software.

FIG. 7 shows an architecture for the software application to run on a computer 700, with capability to backup data to the cloud. The benefit of this configuration is that a user can interact directly with the data that the cameras are capturing through the software user interface 706. The device manager 704 handles different sensor data input streams 702. For example, a USB depth camera has both an RGB color feed and a stereo depth feed. The Device Manager is built with compatibility for each type of sensor input. This allows the overall software application to work whether it is an Intel RealSense stereo camera plugged in, or a simple RGB color camera. The Device Manager keeps track of each device's serial numbers, refreshes the USB connections, and routes the camera feeds or data streams to the software (FloVision) layer 708. It also tracks health, temperature, and other diagnostics of the devices.

The software (FloVision) layer 708 is the core software product offered by the system (FloWaste). This layer is where all data capture and analysis is handled. Images are processed to detect and classify objects, calculate dimensions, measure volume, among other things. Data logging here can be used to measure performance, track results, and report them outside of the application for auditing and tracking.

The User Interface 706 is the front-end of the application, and in the example, is the screen of the user's laptop. From the User Interface, the user can manually collect data from the input sensors/cameras, or choose to run an automatic data collection session. They can view previous sessions data and manage the devices from here as well, resetting the USB connections, or monitoring the live data feed for irregularities.

The Service Layer 710 acts as an intermediary between the modules of the application, like a communicate hub. Requests are sent to the service API and from there they are passed to the required module. For example, images captured are sent by the device manager to the service API where it is routed to software (FloVision) for image processing. It performs database queries, gathering data required by other layers and communicating it out, such as prior calibration results, or customer specific configurations.

The customer database 712 stores assets (image frames, depth frames, other sensor information, customer metadata) and stores ML predictions results. This database can be both cloud-hosted and on the device, with the ability to update the FloWaste food waste analytics dashboard. The analytics dashboard is a web application that the customer can access separate from the software (FloVision), and provides an overview report and analysis of the data that FloWaste collects.

Figure 8:
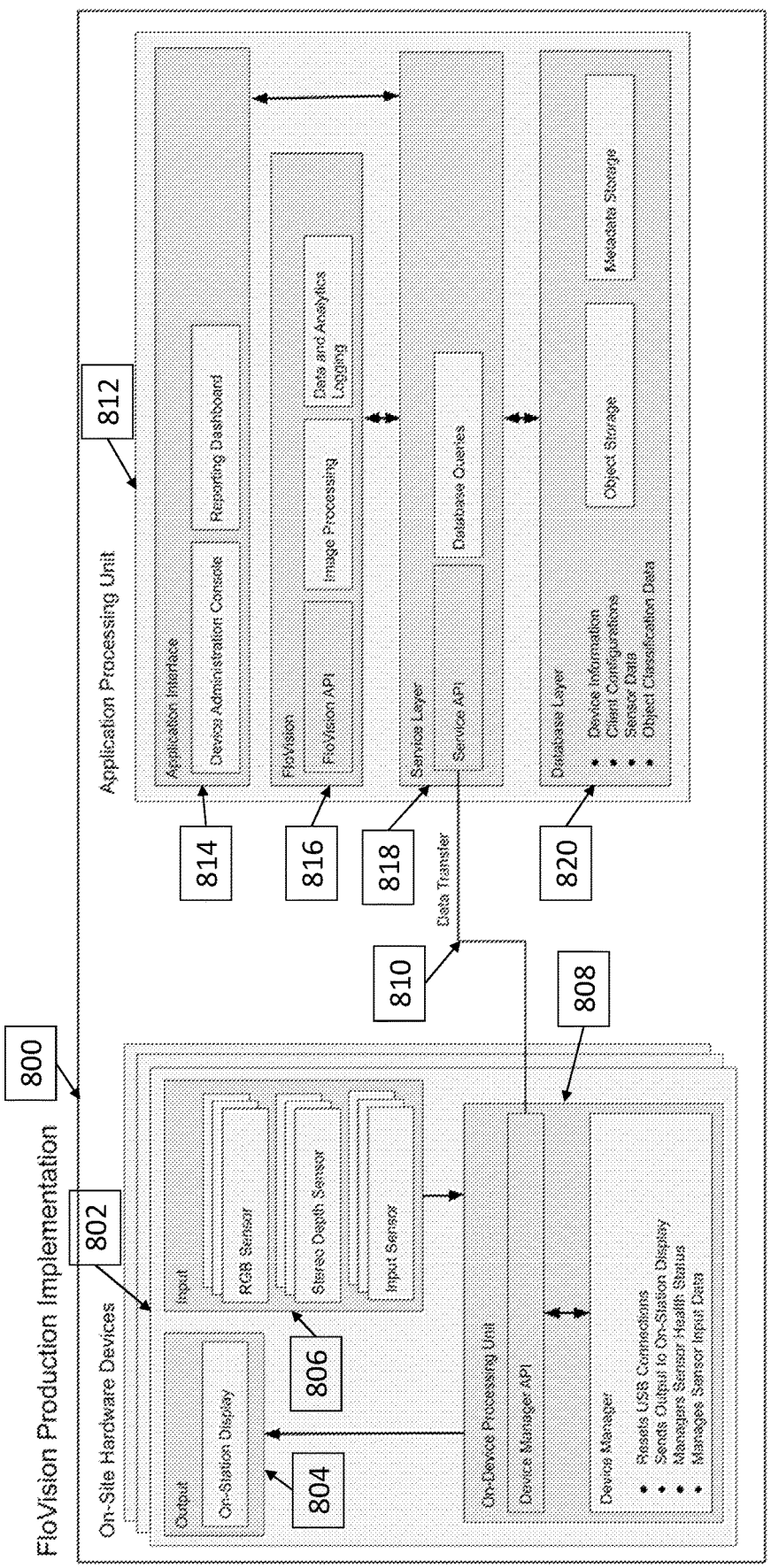
FIG. 8 shows production level implementation of system and process.

FIG. 8 shows software (FloVision) production implementation 800 is an architecture for devices installed at customer locations that could include cafeterias, restaurants, or food processing plants. Here is an architecture for devices installed at customer locations like a cafeteria or restaurant. Here, the hardware is only the camera sensors, sometimes with a depth sensor. Sometimes with additional sensors like a load cell and a raspberry pi or similar processor running the software application. The user interface is only the FloWaste analytics dashboard as a web application, and completely independent from the hardware installation. The user does not have the ability to manually adjust data capture in this configuration. The main difference is that the core software (FloVision) is running on a raspberry pi or similar processor, instead of as a local application on the customer's laptop. The hardware devices 802 consist of input and output modules and an on-device processing unit. The output 804 is an on-station display for users assisted by the software (FloVision) production implementation. The input 806 consists of an array of sensors, including RGB, stereo, infrared, and others. This sensor array provides data requested by the device manager within the On-Device Processing Unit 808. The unit houses the device manager which maintains and gathers data from the sensor array, outputting client-specific results to output display. It tracks engineering diagnostics about the I/O streams and internals for the processing unit. Data sent to the processing unit is then moved through the Service Layer 818 via data transfer 810. The data transfer occurs over intra- or internet to the Service Layer found within the main Application Processing Unit 812. The application interface layer 814 houses device authentication console and reporting dashboard. The architecture of the application processing unit allows quick scaling of the application to all sizes of clients, taking advantage of powerful cloud and/or client servers. The Service Layer 818 then accepts the data and sends it to the required module in the application processing unit. Data sent to the Database Layer 820 is saved to object storage and metadata buckets. Stored data could include sensor data, device information, client configurations, and object classification data. Data sent to the software (FloVision) Layer 816 is processed by the core of the software. The images can be processed for object classification and measurement algorithms to determine volume, mass, and density. This step is unique to each client. Data and analytics are also saved for auditing and reporting purposes, allowing current and accurate feedback from the client solution. The Application Interface 812 allows the client or FloWaste user to manage the active hardware devices from anywhere, see current snapshots of the data recorded, and see reports specific to the clients' needs.

Figure 9:
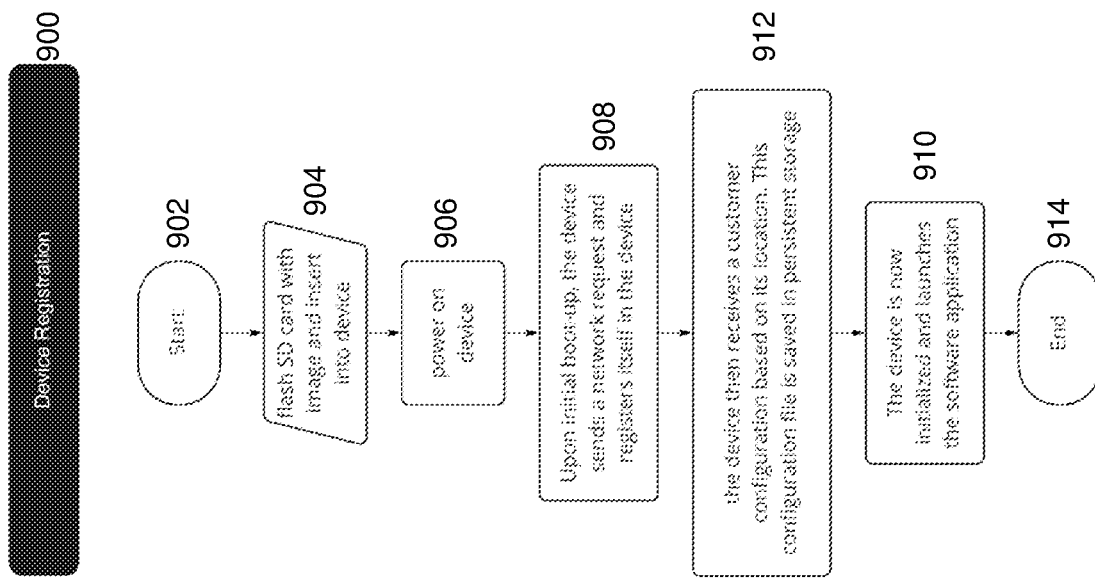
FIG. 9 shows a flow chart of device registration.

FIG. 9 shows device registration 900 describes the process of initializing and registering devices on the cloud backend once the devices are installed at customer locations. Gather materials (902) is done in this step. A micro-SD card is used to store the processor image and persistent data generated by the application. Using an etcher software application (904), flash the micro-SD card with a linux image and insert into the device. The image contains instructions to build a Docker container that holds the application software code. The application code is structured to start the application container on device boot up.

Inserting the SD card (906) into the device's micro-SD card holder and power on the device. In step 908, the first time the device is powered on, the software has instructions to send an API request to the software (FloVision) API backend to register itself on the cloud device registry. Using geographic fencing (912), the device knows what location it is installed in, and assigns itself to a customer registry based on that information. The API request returns a response consisting of a configuration file that is saved to the persistent disk storage (micro-SD card) on the device.

The device (910) is now initialized and launches the software application. The next time the device is booted up, it checks that it is registered to a device registry, and then launches the software application using the saved customer configuration file. The process terminates at step 914.

Figure 10:
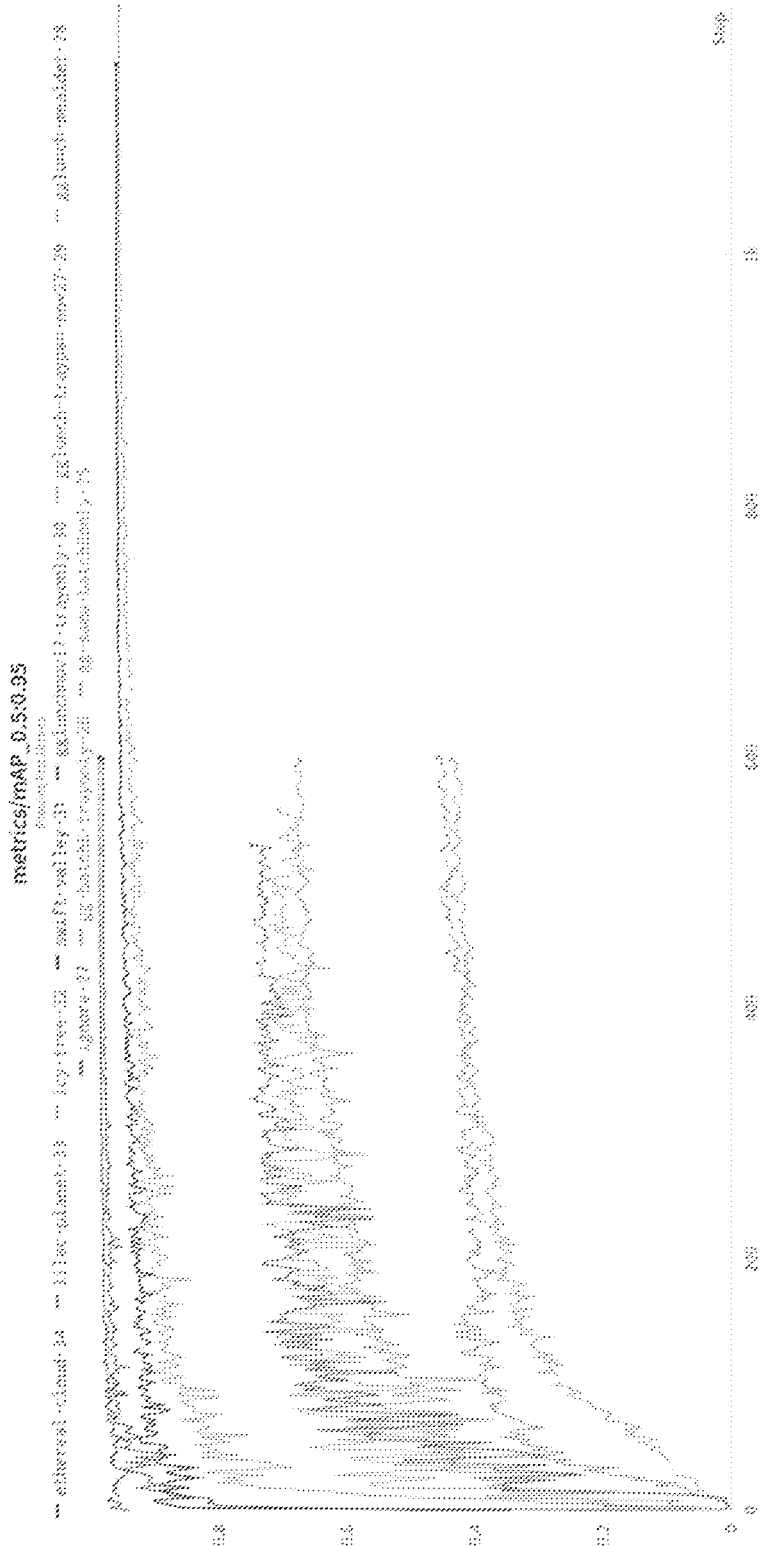
FIG. 10 shows a graph of mAP after training flow.

FIG. 10 shows Object Detection—Training Flow: mAP graph results of 10 iteration runs. This figure is a graph plotting the mAP (mean average precision) of a model through a training run. Each sweep (e.g. gg-batch8-trayonly-26) is a model training run with input parameters. This plot shows how, based on the initial data seeded and parameters chosen, some models reach a higher level of mAP (vertical axis). The horizontal axis shows the number of training epochs chosen. Looking at this graph, most training optimization occurs before 600 epochs. This corresponds to the iterative feedback loop in FIG. 11 (1112->1114->1116). Example of programs that can be used are: YOLOv5 is a family of object detection architectures and models pre-trained on the COCO dataset, optimized for solving object detection problems. The YOLO algorithm is popular due to its speed and accuracy in detecting objects in a frame. YOLOv5 has support for PyTorch, which allows for ease of development. It also has built-in Weights&Biases component to allow one to view the training results interactively. FIG. 10 is an example. One can view the mAP, precision, recall, and mAP_0.5:0.95 (four common metrics for object detection) for each training set. YOLOv5 is just one example of a suitable object detection architecture. Other architectures include YOLOX, mask-RCNN, faster-RCNN, and ensemble learning, where multiple models are chained together.

Figure 11:
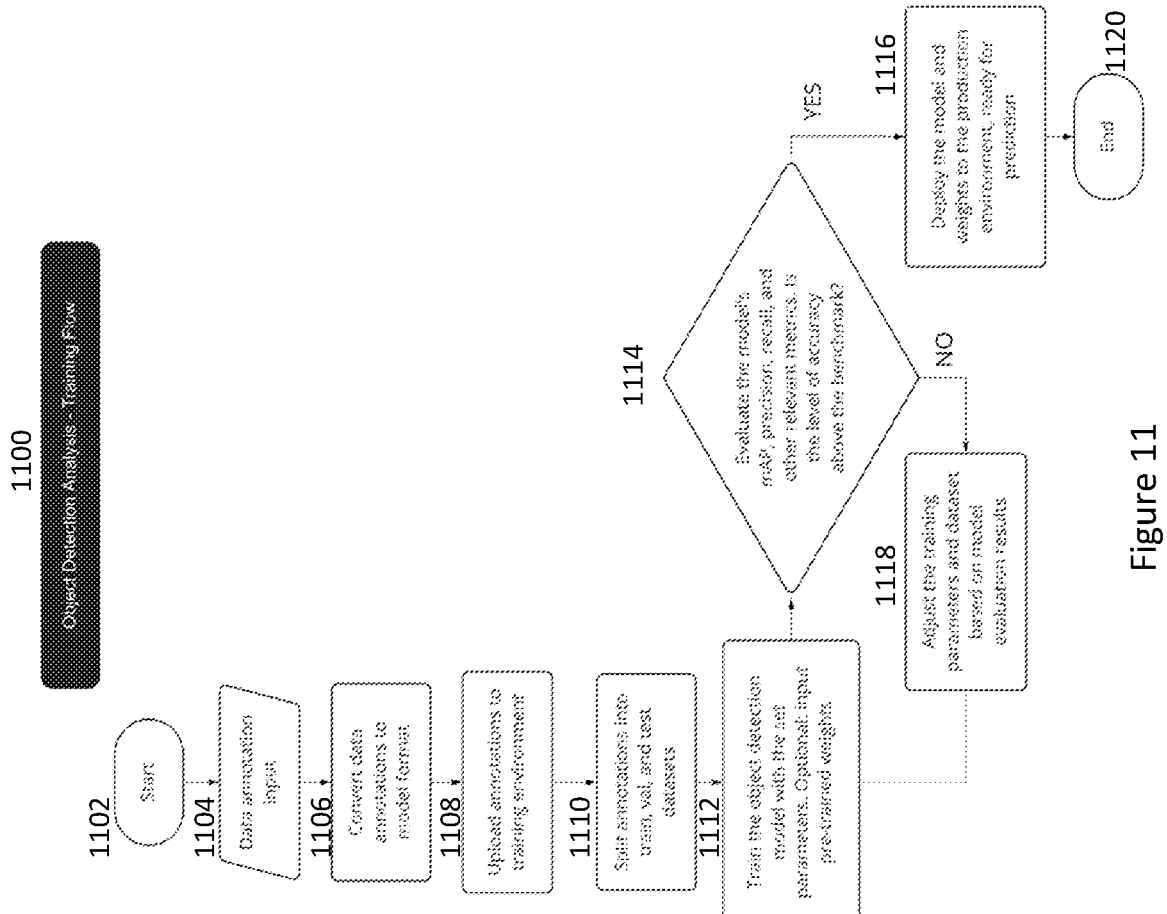
FIG. 11 shows food object detection analysis training flow.

FIG. 11 shows Object Detection Analysis-Training Flow (1100). After a model architecture is selected, the following iterative process is implemented to train the model. Once the model passes the evaluation benchmarks set (mean average precision, or mAP, precision, and recall), then it may be saved and built for a production environment. This flowchart demonstrates all of the work required to train and evaluate a model before it is fit to deploy to a production environment. This is a supervised learning method, meaning that a dataset is prepared with bounding box annotations to directly train the model. This flowchart gives an overview of the model training process to develop machine learning models with high accuracy. The process and method begins (1102) to download data annotations (1104) from Flo-Waste's internal database. Annotations are bounding box coordinates with corresponding food labels tied to an image file. There is a bounding box (e.g. (xmin, ymin), (xmax, ymax) points) for each food object identified in the image.

Sometimes, the input data annotations 1106 are in polygon shape format instead of bounding boxes. Convert the polygon points to bounding boxes by finding the maximum width and height of the polygon as the width and height of the resulting bounding box. Step 1108 shows input data annotations into the development environment folder. This folder includes the model and starter scripts to load in the data to the model.

Step 1110 shows split the annotations between train, validation, and testing datasets. Training the object detection model (1112) with the set data input parameters (the "train" annotation set). Once the model is trained 1114, run it on the "validation" dataset. If the desired accuracy threshold (1116) is achieved, then deploy the model and weights to the production environment. The model is now ready to received prediction requests from data collected from devices at live customer locations. If the desired accuracy threshold is not achieved (1118), identify the edge cases that the model did not properly classify. Adjust the training parameters based on these results, and restart the training process (1112). This is an iterative feedback process. Once the model is hosted (1120) in the production environment, the training process is complete.

Figure 12:
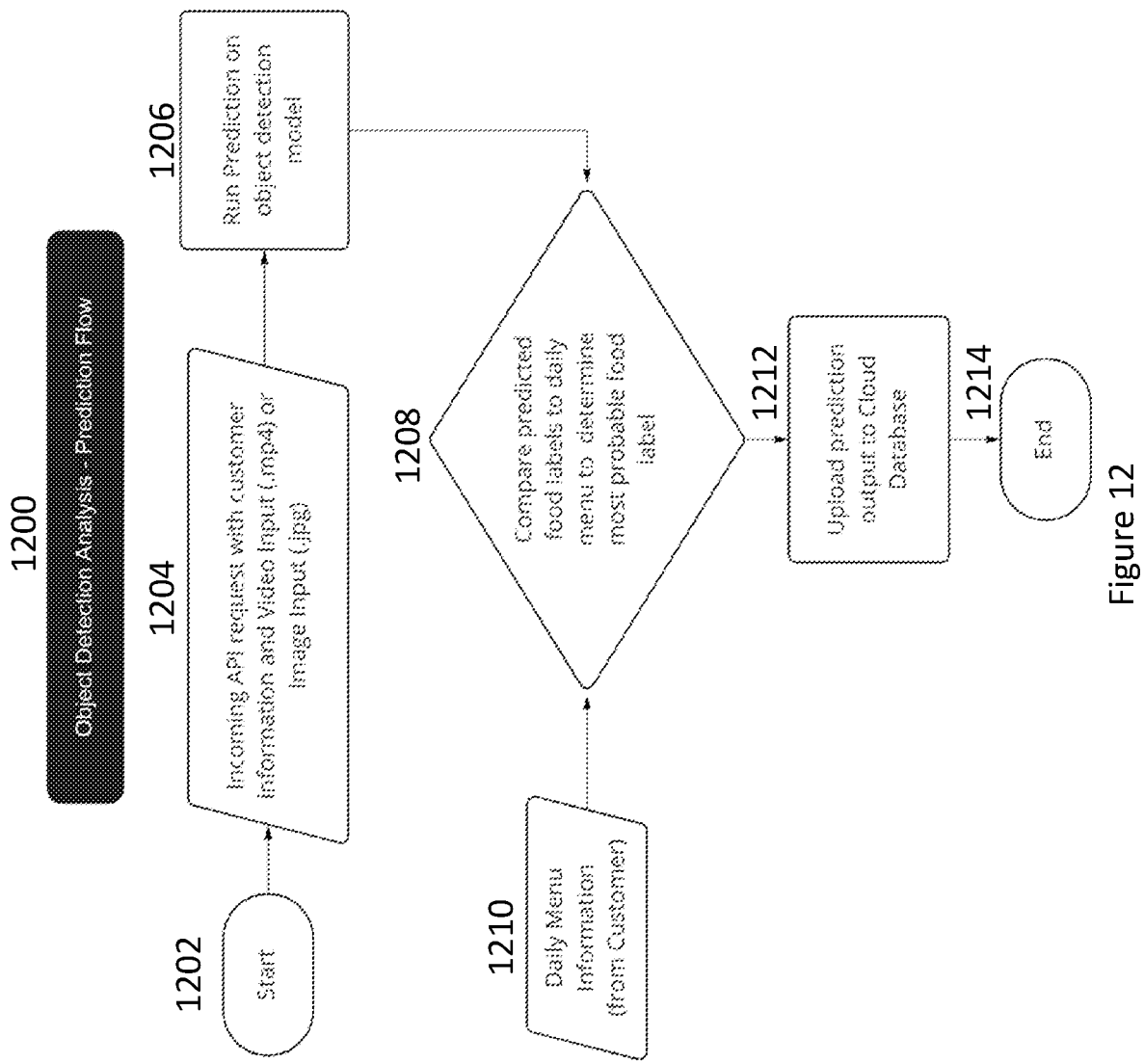
FIG. 12 shows food object prediction flow.

FIG. 12 shows object detection is a machine learning problem that involves classifying objects in images (1200). After model is fully trained, the model and its weights are saved and deployed to the software production environment on the cloud. Here, the model is available for receiving API call to make a prediction request. The API call includes a location of the input data, which can be either a video or image file. The model then runs a prediction on the input data, and produces a result. The algorithm then compares the result and the confidence level with the menu information from the day. Using this filter, the algorithm then selects the most likely food_label present and then uploads it to the cloud database provisioned for the customer. FloWaste owns this data, and uses this to build the predictive analytics component of the UI to deliver to the customer. The output of an object detection model is an object label and position tied to an image. Step 1202 shows start of the object detection prediction flow analysis. The starting point is in the production environment. This is where production models are hosted and ready to received prediction requests from the software (FloVision) API. Input a video or image file through the API request is done at step 1204. Based on where the request is originating from, we know the corresponding customer and can relate it to the specific client module 616.

Step (1206) shows Run prediction on the object detection model built for that customer. The model prediction results returns the top likely foods and their confidence score. At step (1208) Using the prediction result from the model, compare the predicted food labels to the customer's daily food menu to determine the most probable food label for each frame (1 frame for an image, multiple frames for a video). Step (1210) shows Return the prediction output result to the API request, and upload the prediction output result to the Cloud Database, logged under the customer project. At step (1210) as discussed in (1208), the daily menu is pulled from the customer information database and used to validate the model prediction result. End prediction flow analysis is ended at step (1212). This analysis deploys a fully trained object detection model to obtain prediction results on customer data on a daily basis. The video or image input is collected at customer locations as described in the "Data Capture" section. This analysis can occur on the device (edge computing), or on a secure cloud server. In either production environment, the final prediction results are uploaded to the Cloud database provisioned by customer. The process ends at step 1214.

Figure 13:
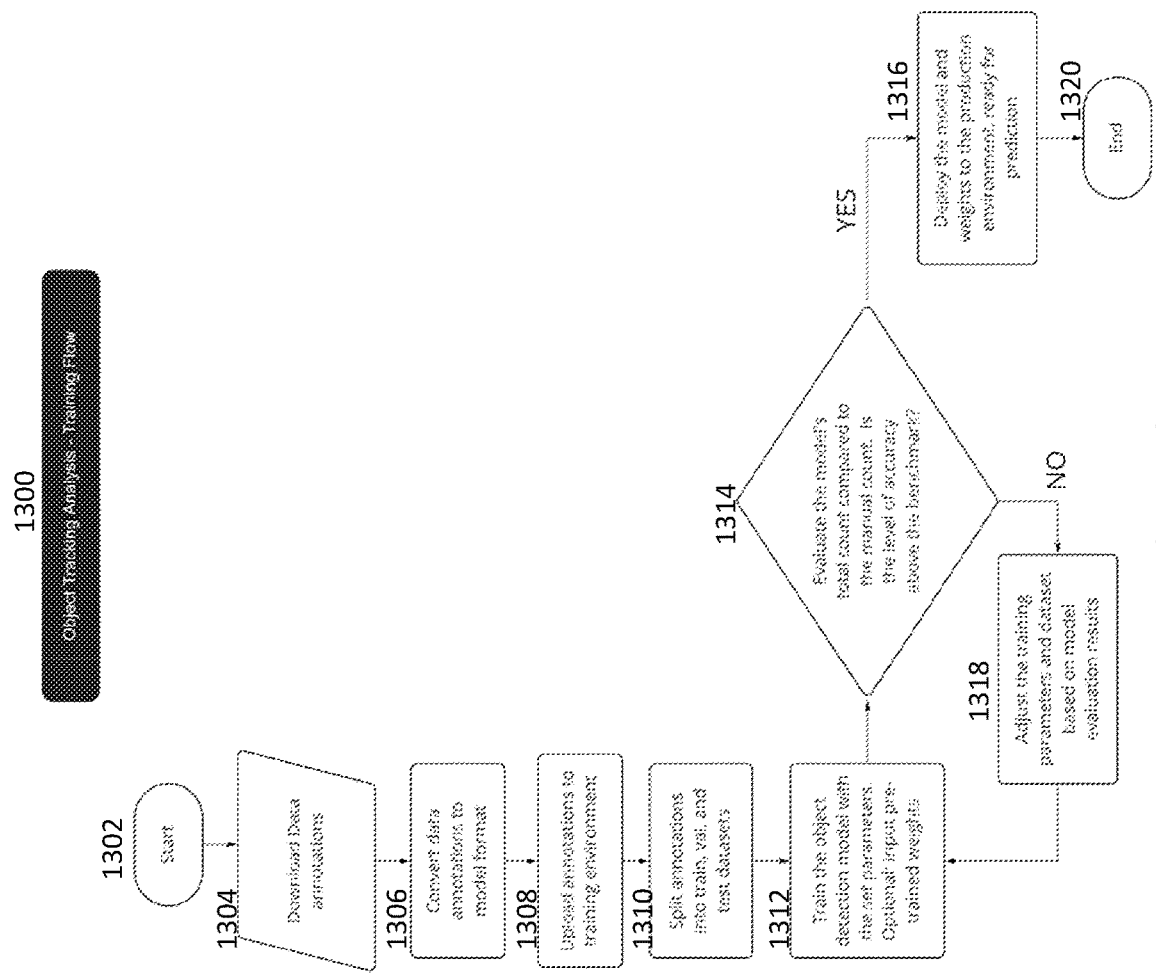
FIG. 13 shows food object tracking analysis training flow.

FIG. 13 shows Object Tracking Analysis—Training Flow (1300). This flowchart gives an overview of the model training process to develop object tracking models with high accuracy. Object tracking is a problem that builds off of object detection. With time-series video or image frames as an input, once an object is detected by a detection model, it can also be tracked as it moves throughout the frames. DeepSort https://github.com/mikel-brostrom/Yolov5_DeepSort_Pytorch is a tracking algorithm that sits on top of YOLOv5 detection models. For object tracking, the development process is very similar to object detection.

Step (1302) shows beginning in a development environment to download data annotations (1304) from FloWaste's internal database. Annotations are bounding box or polygons coordinates with corresponding food labels tied to an image file. There is a bounding box or polygon (e.g. (xmin, ymin), (xmax, ymax) points) for each food object identified in the image. A human manual count is conducted on the "validation" dataset to determine what the true result should be. Does the model's total object count match the manual object count within the desired level of accuracy?

Step (1306) shows the input data annotations are in polygon shape format instead of bounding boxes. Convert the polygon points to bounding boxes by finding the maximum width and height of the polygon as the width and height of the resulting bounding box. Step (1308) shows one input data annotations into the development environment folder. This folder includes the model and starter scripts to load in the data to the model. In the next step (1310) Split the annotations between train, validation, and testing datasets.

In step (1312) training the object detection model with the set data input parameters (the "train" annotation set). As shown in step (1314) once the model is trained, run it on the "validation" dataset. A human manual count is conducted on the "validation" dataset to determine what the true result should be. Does the model's total object count match the manual object count within the desired level of accuracy?

The step (1316) shows if the desired accuracy threshold is achieved, then deploy the model and weights to the production environment. The model is now ready to received prediction requests from data collected from devices at live customer locations. As an alternate in step (1318) if the desired accuracy threshold is not achieved, identify the edge cases that the model did not properly classify. Adjust the training parameters based on these results, and restart the training process (1312). This is an iterative feedback process. Step (1320) concludes once the model is hosted in the production environment, the training process is complete.

Figure 14:
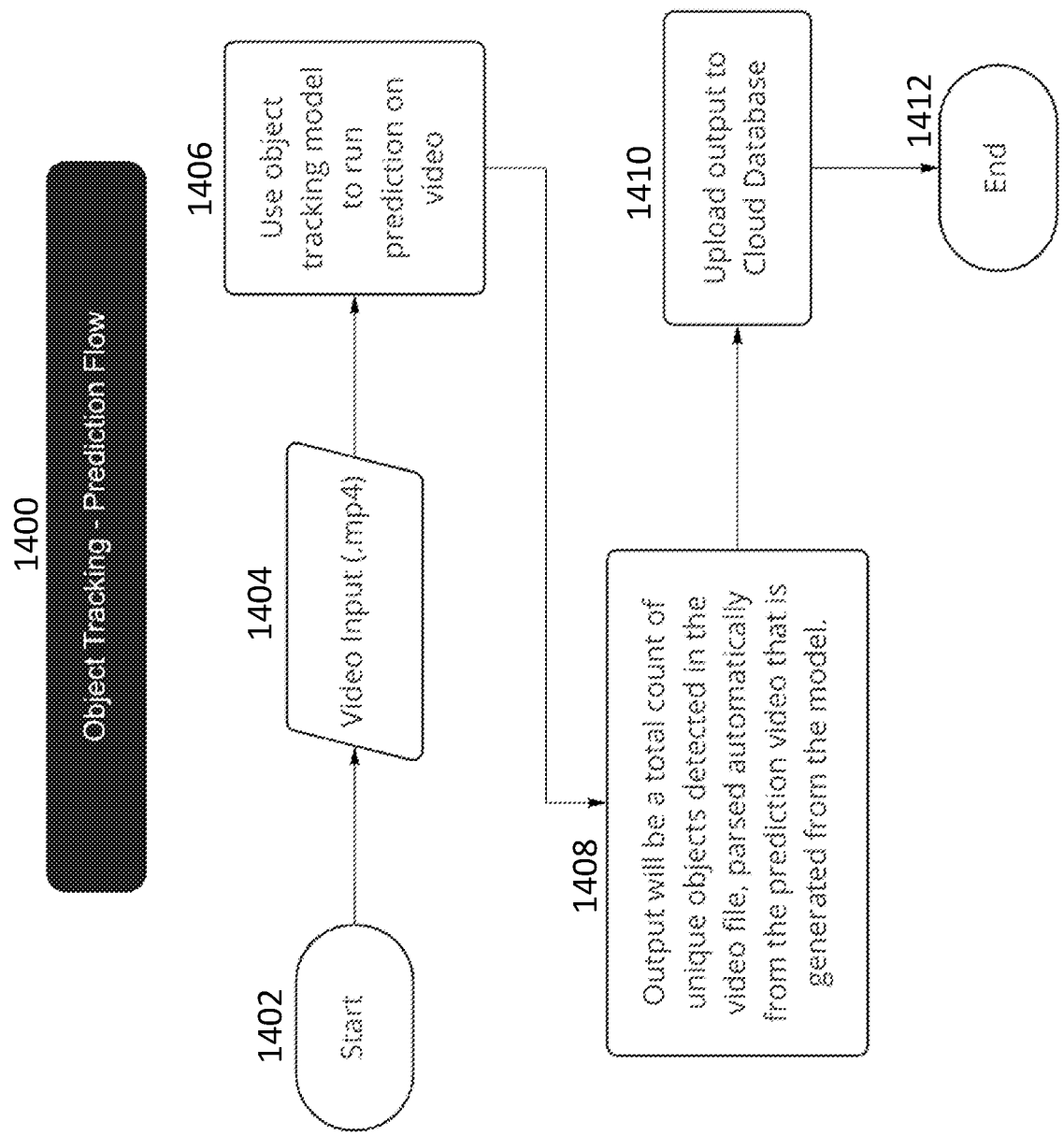
FIG. 14 shows food object tracking analysis prediction flow.

FIG. 14 shows the process flow for object tracking predictions (1400). Many object tracking algorithms are subject to over counting. To adjust for this error, we have identified several different edge cases and created post-processing tweaks to handle each edge case. An object tracking model is a model that is trained to recognize (image classification) and track objects throughout a video scene.

Step (1402) starts Object Tracking prediction flow analysis. The starting point is in the production environment. This is where production models are hosted and ready to received prediction requests from the software (FloVision) API. Step (1404) gathers an input a video file through the API request. Based on where the request is originating from, we know the corresponding customer. Step (1406) shows run prediction on the object tracking model built for that customer. Step (1408) shows calculation of the model prediction returns as a result of a total count of unique objects detected in the video file. The total count is a summation of unique objects found in the prediction video output generated by the model. At step (1410) the output is saved to the software (FloVision) cloud database with relevant customer information. At step 1412 object tracking prediction flow is stopped.

Mass calculation using volume and density at an industrial setting requires the following considerations:

- Depth data and identification data are used as inputs to calculate mass.
- Depth data can be captured using stereo camera(s), TOF sensors, LiDAR, RADAR, laser gate, or penetrative volumetric sensors (MRI, CT, X-Ray) but not limited to these sensors.
- Identification data can be captured using visual imagery (RGB, HSV, CIELAB, or other), hyperspectral imagery (including NIR), CT, MRI, X-Ray, Ultrasound scanning.
- Depth data is converted into a 3D point cloud structured array.
- Identification data is used to find the area of interest in the 3D point cloud. This is the area that contains the food object and is referred to as "object point cloud". Change in depth data can also be used to find the area of interest.
- The object point cloud can be segmented into relevant shapes. These idealized shapes are dependent on the object identification e.g. breadstick is similar to a cylinder. If you cut a cylinder along the axis you create two hemicylinders. This is advantageous for certain volume calculation methods.
- Use a specified volume calculation method (e.g. Delaney Triangulation or convex hull approximation) to calculate the volume of the segmented shapes (e.g. the two segments of the breadstick).
- Add the segmented volumes to get the total volume estimate.
- Evaluate if this estimate is within an expected range for the given object. If the volume is outside of this range, use a different volume calculation method on the segmented shapes. The expected range for the given object is based on experimental data gathered from known objects.
- If the volume is within the expected range, use the object identification to find the density in the FloWaste density lookup table.
- Multiplying the Volume by the Density gives the Mass estimate of the object, which can be stored for later analysis.

Figure 15:
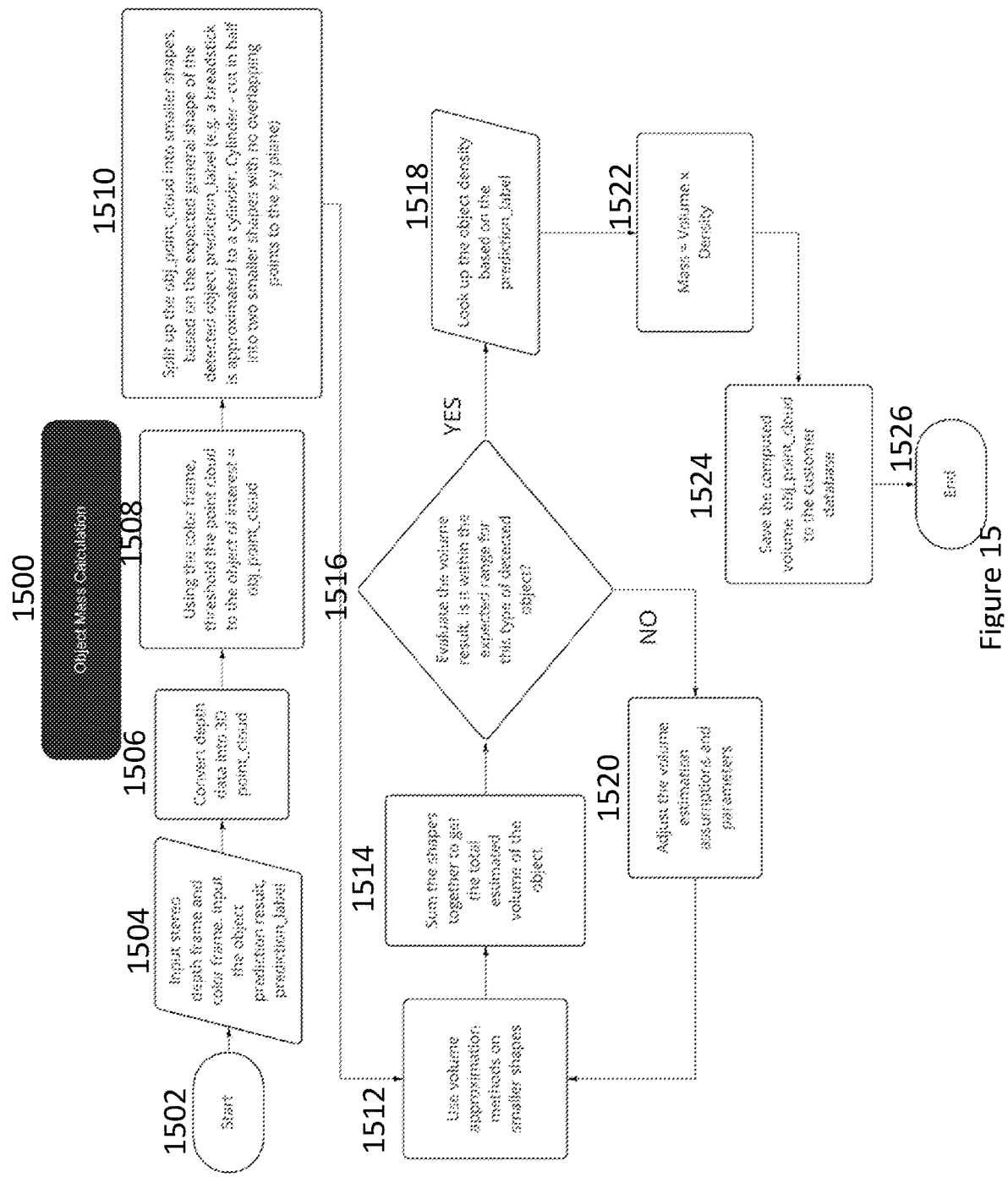
FIG. 15 shows food object mass calculation flow.

FIG. 15 shows (1500) overview of Object Mass Calculation method by beginning the method and process at step (1502). This takes place at "Data logging and analysis" (816) of software (FloVision) API and at step (1504) input is recorded as a depth frame array and color frame array from stereo camera sensor. Another input is used from step 1210 as the object prediction result (i.e. prediction_label=steak, confidence=93%, bounding_box coordinates), step (1506) converts the depth array into a point cloud (points in 3D meter space). Using the color frame array (1508), crop the point cloud to the object of interest by using the object bounding box coordinates from (1504). The output is only the points associated with the object of interest, labelled "obj_point_cloud".

Split up the obj_point_cloud (1510) into smaller shapes is done, based on the expected general shape of the detected object prediction_label. For example, a breadstick is the approximated shape of a cylinder. To use a 2D volume estimation on the shape, break down the shape into smaller sub-shapes so that for each sub-shape, there are no overlapping points to the x-y plane. At step (1512) for each sub-shape, perform a volume approximation method to output the volume of each sub-shape. At step (1514) sum the volumes of the sub-shapes to get the total volume estimate of the object shape is calculated. Evaluation the volume result for the object (1516) is performed. Is the result within the expected range for this type of detected object?

If yes (1518), save the volume (object_volume) and look up the density of the object based on the prediction_label. (object_density). If no (1520), adjust the volume estimation assumptions and parameters. The mass of the object is equal to the object_volume times the object_density is calculated in step (1522). At step (1524) Save the object_volume and the obj_point_cloud to the customer database and end the process at step (1526).

Figure 16:
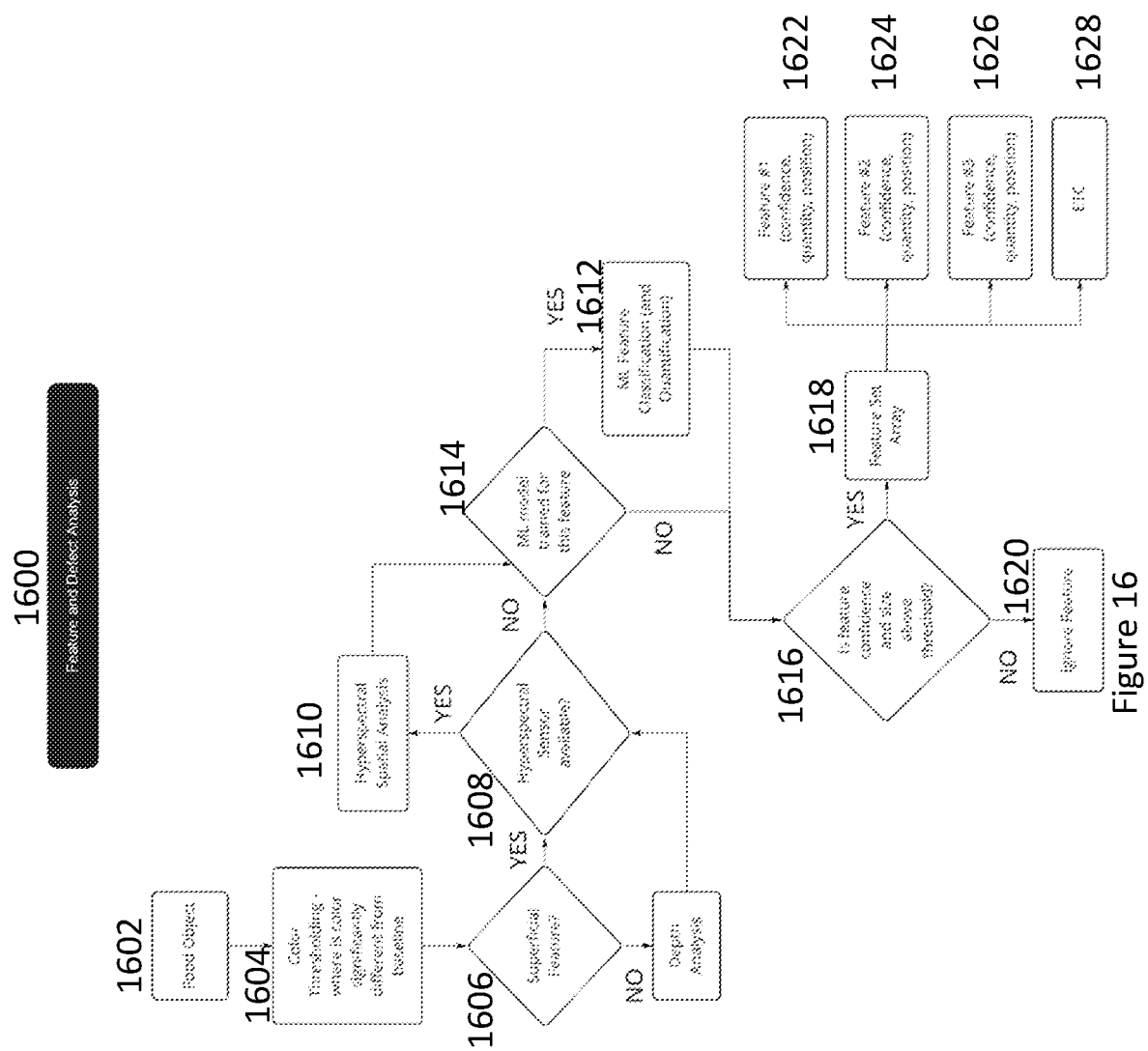
FIG. 16 shows food object feature and defect analysis flow.

FIG. 16 shows a known food object (1602) can be analyzed for features and defects (e.g. bruises, processing errors, cuts, ageing, ripening, lumps, craters, etc.) (1600). Spotting Features, Defects, and Quality Assurance Analysis: In specific applications, food features and defects are recognized or analyzed. This can follow identification of food, or be completely independent if the food is already known, depending on the context. Feature and defect analysis uses proprietary algorithms and data sets to identify the feature in question. Examples of features that are analyzed in animal proteins include: backstrap length, side muscle ("tail") length, other muscle dimensions, fat wedge size, Intermuscular Fat ("marbling") quantity, trimming defects (e.g. holes or "windows" in outer backfat where fat has been over-trimmed to expose lean below), excess protein wasted (lean remaining on bones or body fat trimmings), discoloration (due to age, environment, etc.). Examples of features that are analyzed in produce and other food production include: bruises, scratches, discoloration, quality, age, texture, and remaining shelf life). This analysis can also be used to assess quality of food products and procedure. If the number of features that relate to bad quality breaches a specified threshold in a given time or quantity, an alert/notification can be sent. This data is also stored for supervisor review at the end of shift, day or other time period.

Standard Color imagery is used to establish changes in color from expectations using thresholding (1604). If the feature is superficial, i.e. a '2-dimensional' feature with no depth, depth analysis (1630) is not required (1606). If the feature is 3-dimensional the depth can be analyzed (1606), which can aid in feature/defect classification and quantification. If hyperspectral sensing is equipped, this analysis can take place (1608). Hyperspectral spatial analysis data can then be used in feature/defect classification and quantification (1610). If a machine learning model has been trained to classify or quantify this feature/defect (1614), that model can now be used in feature/defect classification and quantification (1612). After these classification methods, the calculated confidence that the feature/defect exists is compared to the threshold (1616). The size of the feature/defect is also compared to a minimum size threshold for relevance.

If both the confidence and size are greater than the thresholds, the feature is added to the Feature Set Array (1618). If either threshold is not met, the feature is ignored (1620). The Feature Set Array consists of all the detected features for this food object (1622, 1624, 1626 and 1628).

Figure 17:
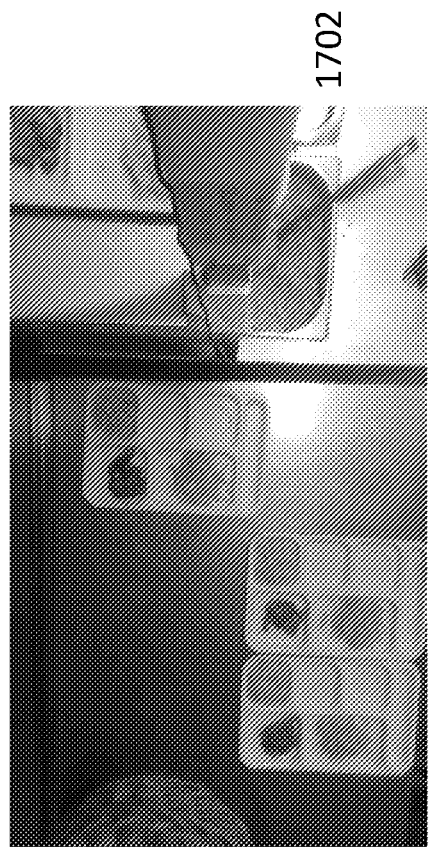
FIG. 17 shows a cafeteria tray being scanned prior to consumption.
Figure 18:
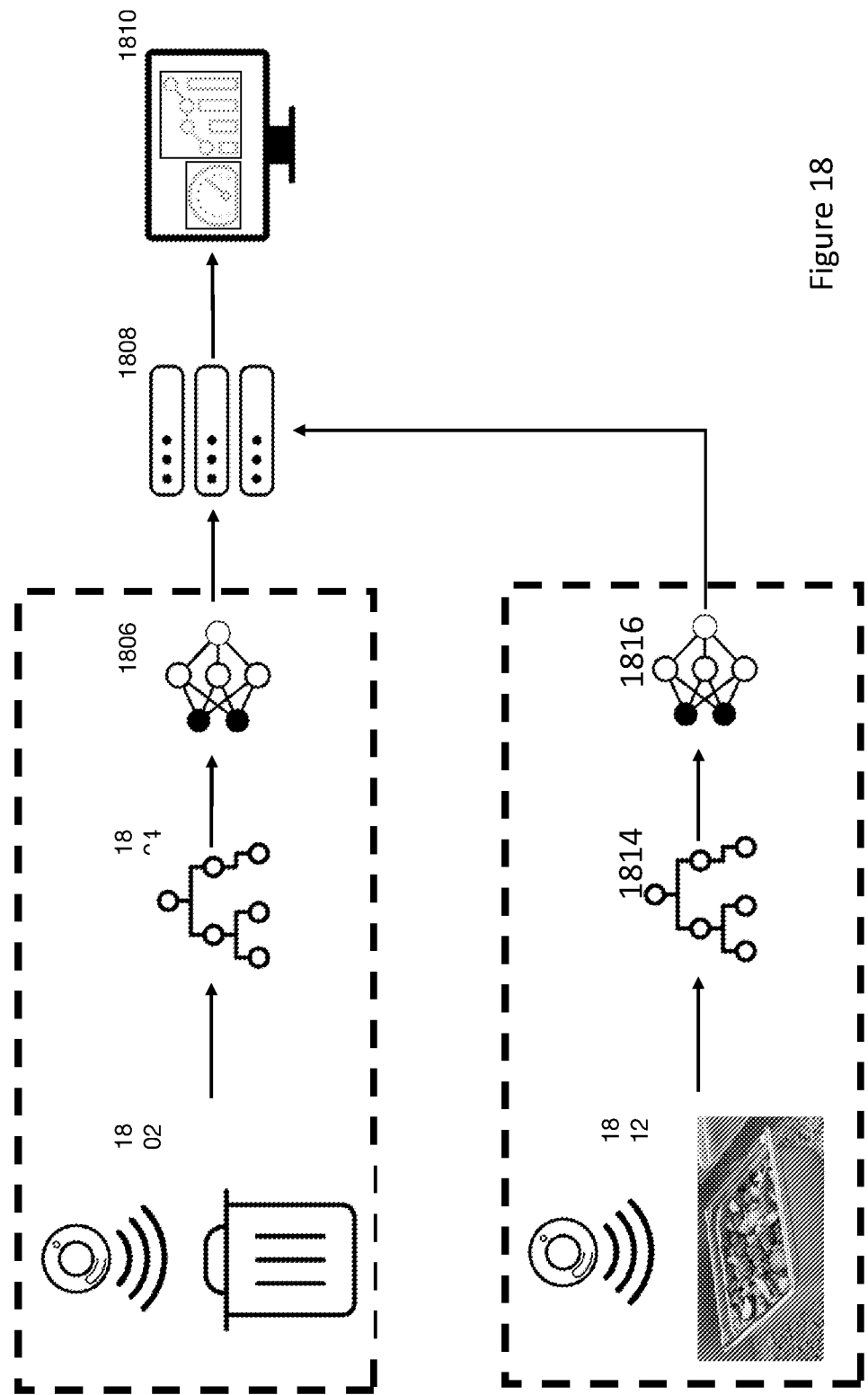
FIG. 18 shows a system that is implemented in a cafeteria, with both front-of-house (consumer facing) and back-of-house (kitchen) data collection stations.

FIG. 17 shows lunch trays or other food objects can be counted and analyzed 1704 at a serving station 1702, or other relevant location. The image acquisition device would be installed right at that station. FIG. 18 outlines multiple data collection points (1802 & 1812) carrying out their individual data capture (1802 & 1812), their individual data processing including volumetric analysis, key dimensioning, and other features (1804 & 1814), and their individual identification and machine learning classification (1806 & 1816). These data collection points could be at different stages of a cooking process, production line, cafeteria line, dining hall, etc. Upon completion of individual processes the data can be stored in a central location (1808). This central location can combine results, and time aggregate data to generate insights and trends. Relevant insights, trends, and data points can be presented to a user (1810).

FIG. 18 also shows a data source to the Post-Consumer waste bin data capturing. First step is a data collection source, a camera unit installed above a post-consumer waste bin or other area, to collect plate scraps after the subject is done eating. Next step is the volume processing software, outlined in Figures before. Next step is the machine learning model that determines the food label automatically, outlined in Figures before. Next step is a cloud server to aggregate, parse, and generate insights based on collected data. Next step shows the client side dashboard, which is how the insights are delivered back to the cafeteria chef to inform their decisions moving forward to reduce food waste. These insights include the likes of portion sizing, preparation changes, ingredient usage, customer feedback, and supplier changes. Next step shows another data collection source, a camera unit installed above a kitchen waste bin to collect prepared kitchen scraps.

Figure 19:
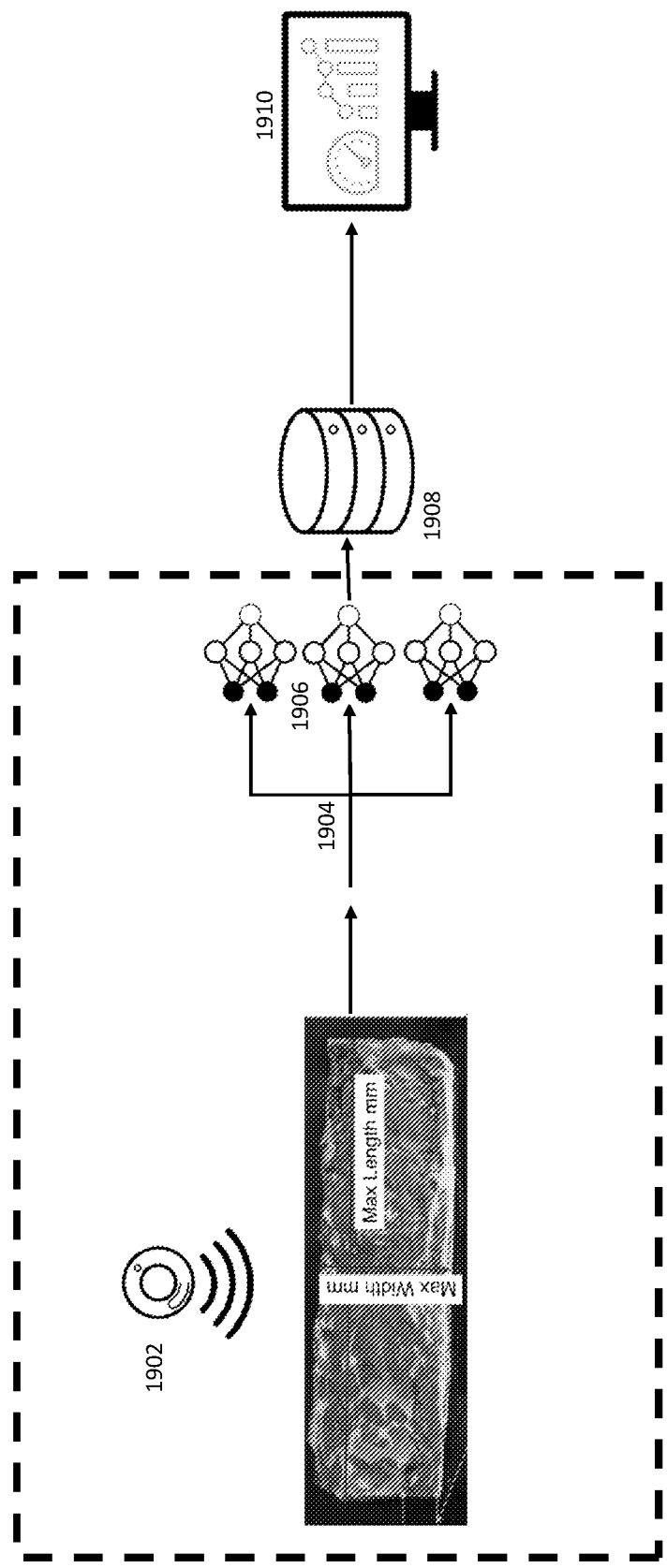
FIG. 19 shows industrial application of system, process and method for food consumption and waste calculation.
Figure 20:
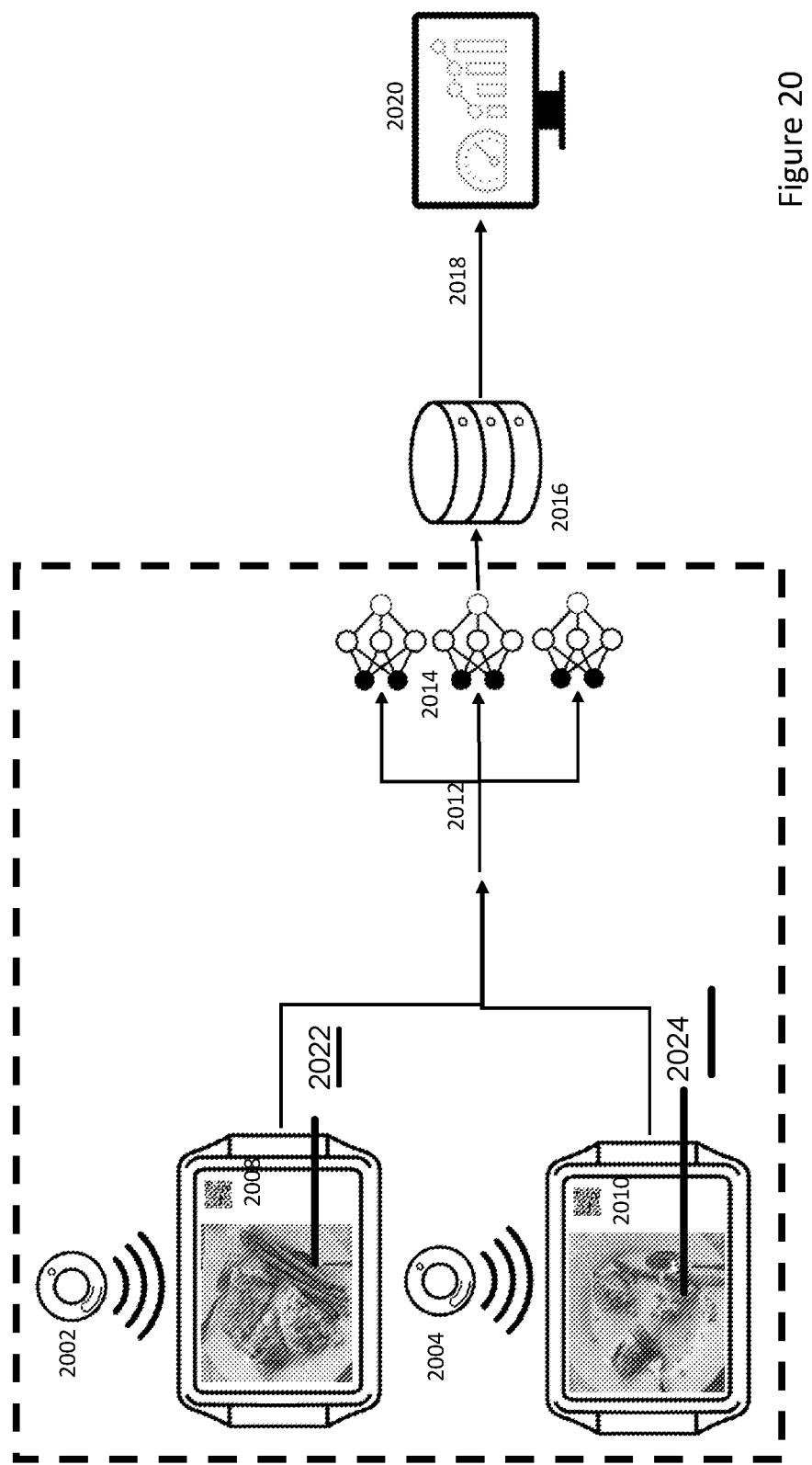
FIG. 20 shows a system that collects individual meal data in a cafeteria setting using camera sensors as a data source.

FIG. 19 shows a sensor, or variety of sensors, capture data on a food object in a food production setting (1902). A computational volume of the food object is created and processed in step 1904. Algorithms and machine learning models are used to calculate dimensions, features and defects, along with classifying the object (1906). The results from these algorithms and models are passed to the analytics module engine, which generates key insights and trends (1908). The user can access aggregated food insights and trends, along with individual data points (1910). FIG. 19 is a graphical method to determine the minimum and maximum dimensions along a given length and width of an object. This uses a color image, along with a conversion from pixel to meters, to determine real-world dimensions of an object. The conversion is supplied by the camera's calibration intrinsic and extrinsic values.
 a) input image
 b) get contour of object from image
 c) get centroid of object
 d) get minimum area rectangle of object. this gives us the box coordinates, along with the major and minor axis vectors
 e) Set major_vector=long side of rectangle
 f) Set minor_vector=short side of rectangle
 g) get major axis start and end point (from major_vector)
 h) get minor axis start and end point (from minor_vector)
 i) take the major_vector, and draw a perpendicular line through the axis, stopping at each edge of the object.
 j) take edge_point_top and edge_point_bottom and compute the distance between them. This is the width of the object w, taken at one point along the major_vector.
 k) Repeat step j for each point along the major_vector. Initialize w_min=image_width. If w<w_min, then set w_min=w. You will end up with the minimum width, minW.
 l) For maximum width, repeat step j for each point along the major_vector. Initialize w_max=0. If w>w_max, then set w_max=w. You will end up with the maximum width, maxW.
 m) repeat steps k-l with the minor_vector to find minL and maxL FIG. 20 shows sensors (2002 & 2004) are used to capture data of food at different times, after a process has occurred (e.g. in a cafeteria before and after a meal has been served (2022) (food object before consumption) and eaten (2024) (food object after consumption), or on a production line before and after trimming). An identifier is used to link the before and after data points, e.g. a QR code, barcode, RFID signal, etc. (2008). In some applications the food itself, or features of the food, are used as the identifier. All data points are processed with a volume generated and calculated, along with the difference between the data points (2012). This process is not limited to 2 data points. Algorithms and machine learning models are used to calculate dimensions, features and defects, along with classifying the objects (2014). The results, including the direct differences between the data points, are passed to the insight engine, which generates key insights and trends (2016). The user can access (2018) aggregated food insights and trends, along with individual data points (2020).

Figure 21:
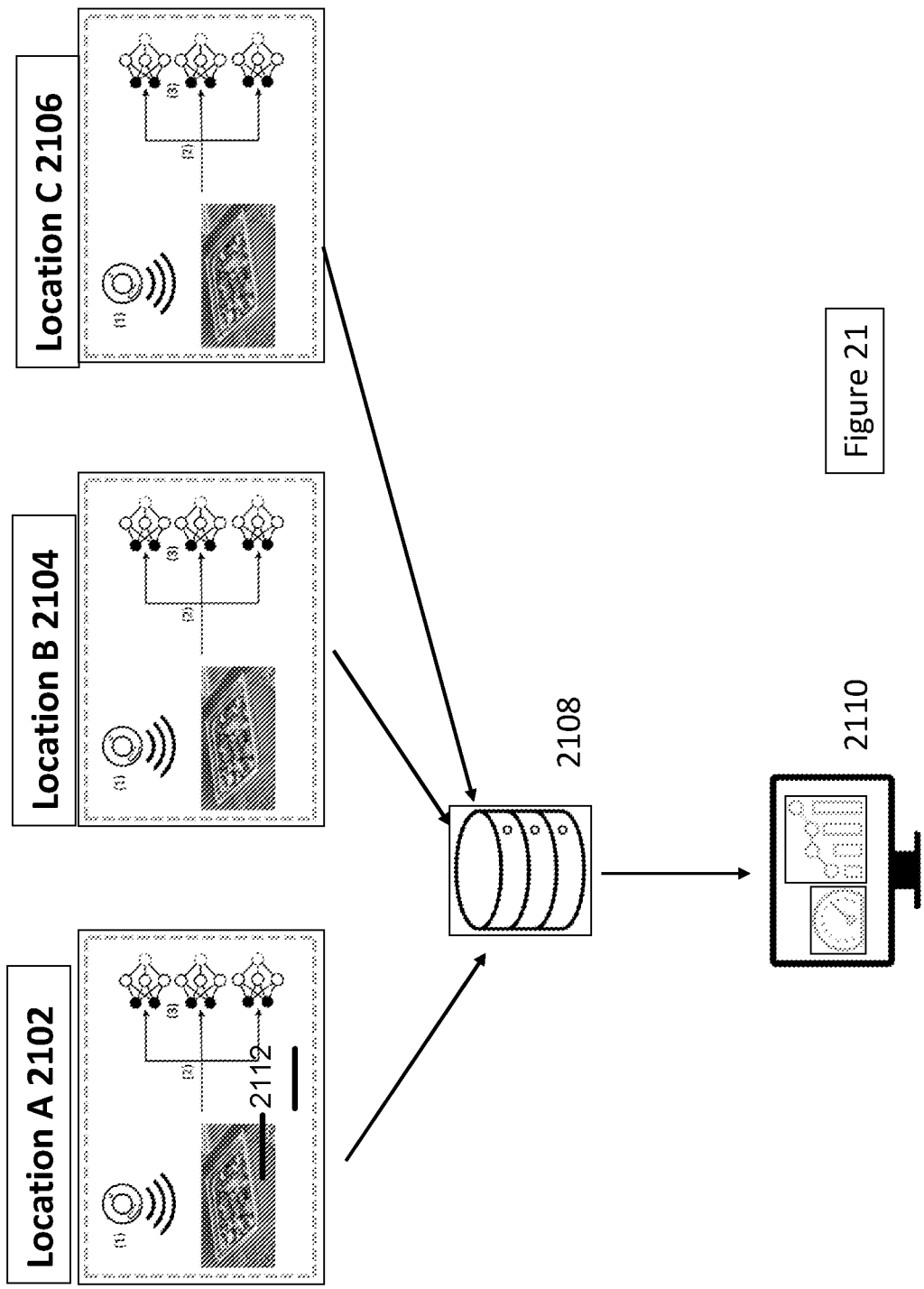
FIG. 21 shows an installation in the back-of-house (kitchen) across multiple restaurant locations to capture food waste and aggregate data from multiple locations.
Figure 22:
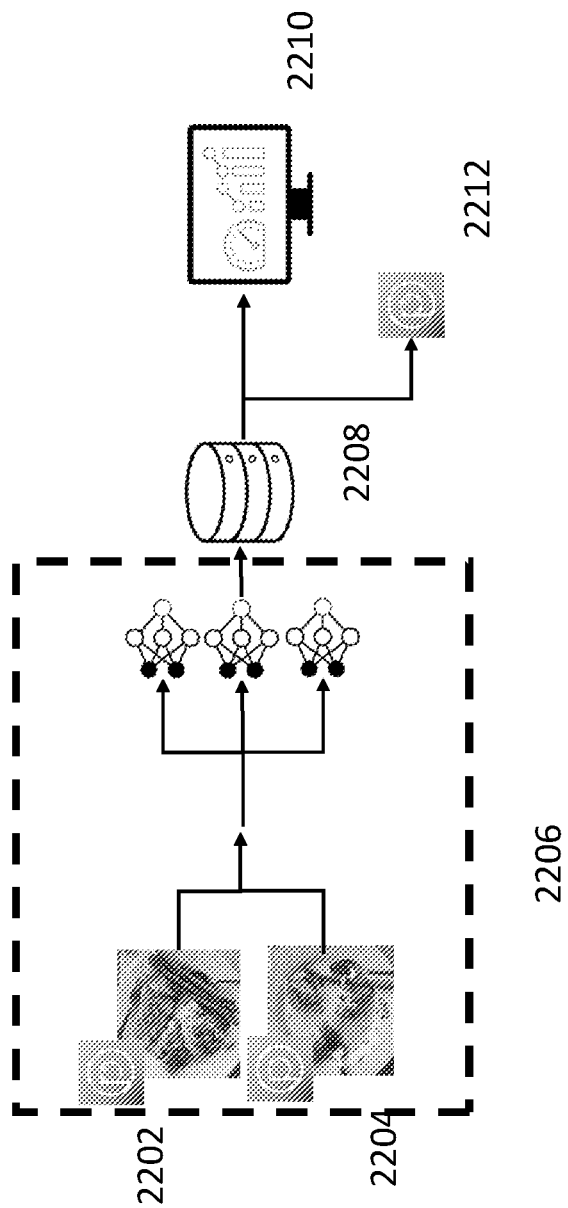
FIG. 22 shows a system that captures individual meal data in a cafeteria setting using a mobile application as a data source.

FIG. 21 shows multiple locations data (2102, 2104 and 2106) can be used by the Insight generation engine (2108). This data can be presented in the form of insights, trends, and key data points in a time aggregated and/or location dependent manner to the user (2110). This applies with sensors across one kitchen or factory, or sensors across a company, country, etc. The system, process and method can be installed in single use or multi use platforms. FIG. 21 shows an installation in the back-of-house (kitchen) across multiple restaurant locations to capture food waste and aggregate data from multiple locations. FIG. 22 shows a mobile application that can be connected for individual use. The app must be downloaded by the individual, who then uploads a photo at the start of their meal from a food storage container (2112), and a second photo when they are done with their meal. Cafeteria locations with instant system, method and process software will have a geofence to capture any data generated from meals eaten at that location. Every time a user successfully documents a meal, they will receive an accurate nutritional breakdown (total calories, carbohydrates, lipids, protein, for each identified food) that can sync with Apple Health or similar Health platforms.

Figure 25A:
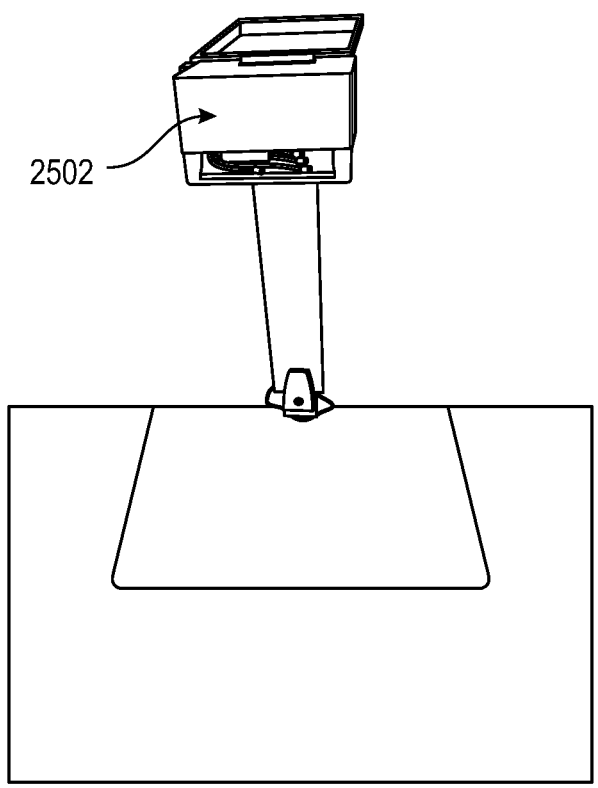
FIG. 25A and FIG. 25B shows a device installed in user space.
Figure 25B:
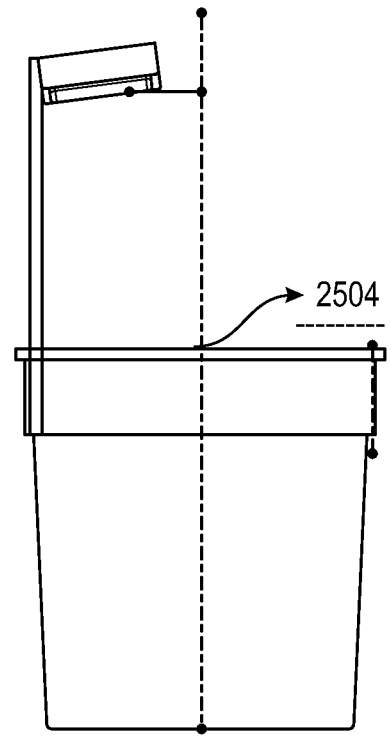

FIG. 25A and FIG. 25B shows an embodiment of the device that is being used. FIG. 25A shows the device (2502) mounted next to a scan table for the food tray to be scanned. FIG. 25B shows the orientation of the light path from the device to the table (2504) below.

FIG. 22 shows a mobile application can be used to gather data before and after a process or meal (2202, 2204). This data can be processed on the device, with a volume generated and calculated, then algorithms and machine learning models used to classify and quantify the food and relevant features (e.g. nutrition) (2206). This data can be sent off device and the insight engine can identify insights and trends (2208). Key trends and insights can be presented to the user in the mobile application, including nutritional breakdown over time, and recommendations (2212). Insights and trends can also be presented to other users with other interface methods (2210).

Figure 23:
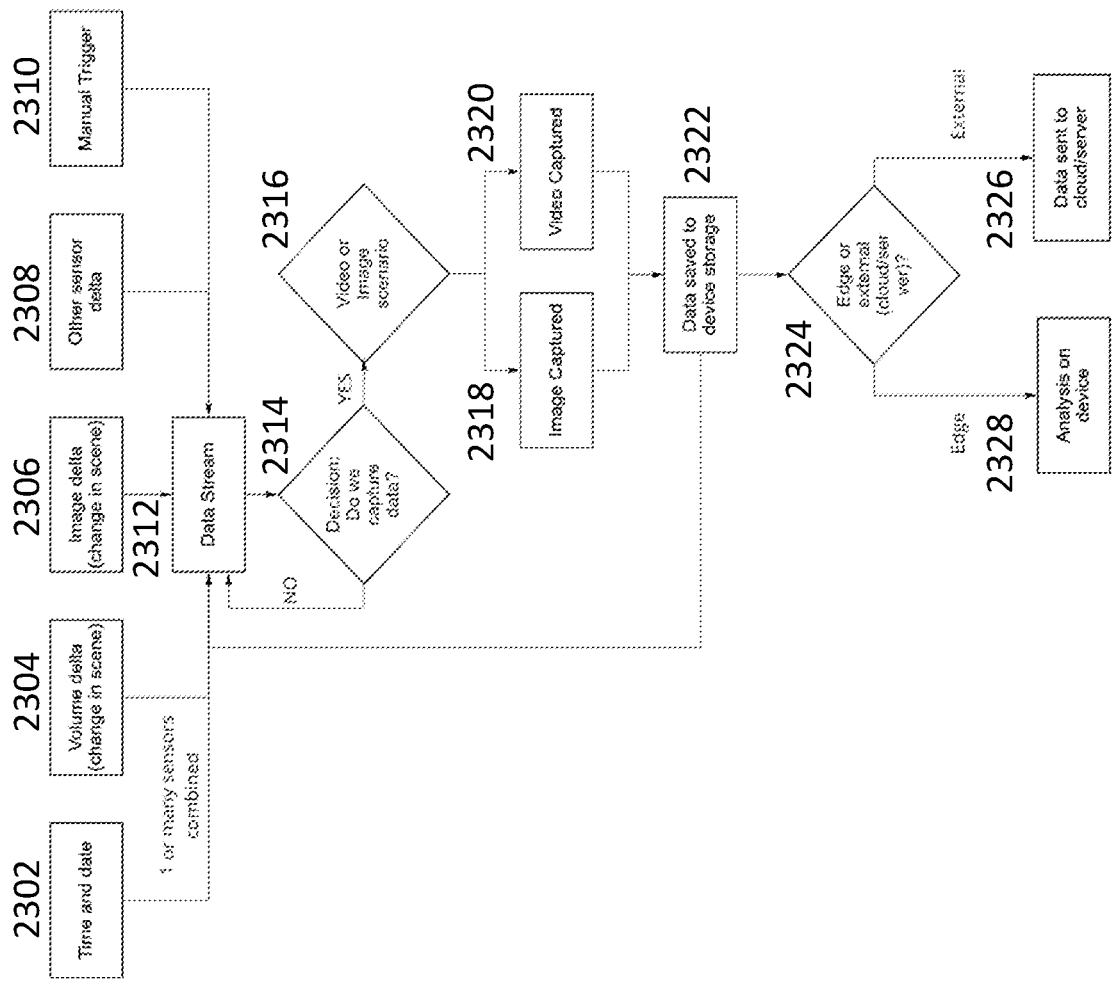
FIG. 23 shows flow chart of process capturing food consumption and food waste using the camera sensor during data collection method.

FIG. 23 shows the decision making process has a complex data stream (2312) as the input and data capturing. A variety of data streams can be used in the decision process to capture data, and what data should be captured. 1 or many of the following data streams can be used:

Time
Date
Manual Trigger (e.g. button)
RGB/HSV/LAB (or other) color Thresholding
Volumetric Thresholding
Load Cell
Machine Learning Model Outputs
Time of Flight (TOF) sensor Thresholding
LiDAR
RADAR
Hyperspectral Thresholding including Near Infrared Thresholding
Laser gate sensor(s)
Density Thresholding This data is used in a decision making algorithm to determine if data should be collected, what method of data collection should be implemented, and what sensors should be used to capture data. Data can be collected discretely (e.g. images) or continuously (e.g. videos), from one or many sensors simultaneously. Data can be streamed to monitoring devices or displays in some applications if a data connection is present.

Data that has been collected is saved by the processor to the device storage. Depending on the application, this data may be sent off the device for analysis, or analyzed on the device by the processor. This data stream is made up of data from a single source or a variety of sources, for example: Time and Date data (2302) from the processor or network, the location, the perceived change in volume within the volume detection sensors area of vision (2304), the perceived change in cosmetic features (e.g. color, brightness, hue) within the camera sensors area of vision (2306), any other sensor that can be used to detect changes (2308), or a manual trigger such as a button, switch, keypad, touchscreen, verbal command, etc. (2310). A decision is then made, based on this data stream (2312), if data should be captured (2314). If the process has decided to capture data (2316), a new decision process is activated; should continuous data (e.g. video) (2320) or discreet data (e.g. image) (2318) be captured (2316). This can depend on the Data Stream (2312), or any other data source. The data that is captured is then saved to storage on the device (2322). A decision making process is activated (2324) to decide if data should be further processed on the edge device (2328), or sent off the device for analysis (2326). This decision making process can depend on the Data Stream (2312), or any other data source. Key dimensions, features, and defects can be captured e.g. width, depth, thickness, angles, color breakdown, shape, volume, cross sectional planes, custom features specific to specific food objects, etc.

Figure 24:
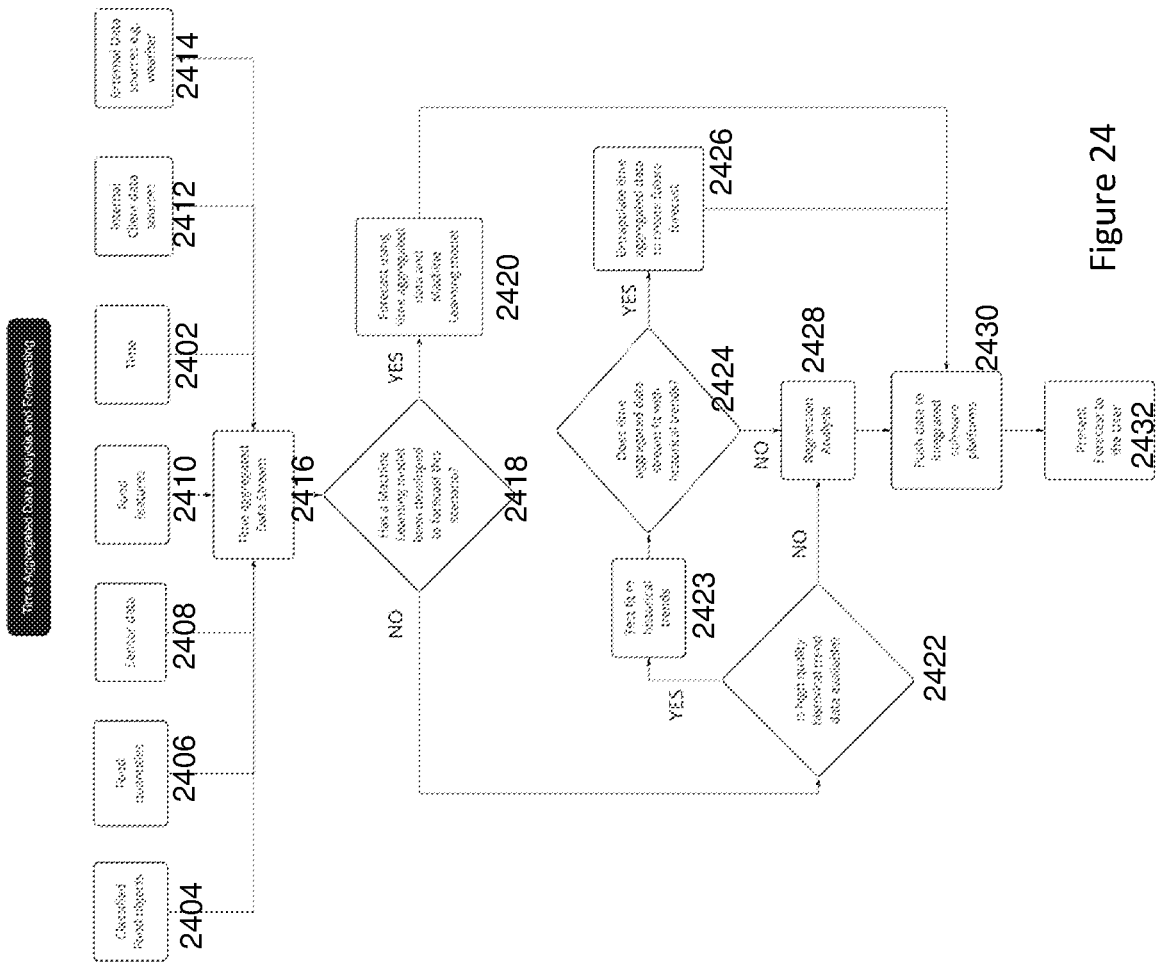
FIG. 24 shows the process for data analysis and forecasting with the use of time aggregated data.

Time Aggregated Data Analysis and Forecasting is shown in FIG. 24. FIG. 24 is a flow chart that shows the process for data analysis and forecasting with the use of time aggregated data. A variety of data sources can be used, including Time (2402), food objects that have been classified/identified (2404), food quantities (including volume, mass, and/or dimensions) (2406), other captured sensor data (2408), food features and/or defects (2410), internal client data sources (stock levels, procurement data, sales, etc.) (2412), and external data sources (weather records, weather forecast, public health guidelines for a geographic location and/or time period, traffic flow, survey data, census data, etc.) (2414). These data sources can be aggregated over time to create a time aggregated data stream (2416). If machine learning models have been developed to analyze and/or forecast the scenario in question, or similar scenario (2418), they are used to analyze and/or forecast the scenario (2420). If not, historical data trends are tested (2423). Data fits, and trends are analyzed to identify similarities (2422). If historical data analysis produces a fit (2424), it can be extrapolated to forecast into the future (2426). If no fit is found, other regression analysis can be performed to analyze and forecast (2428). All of these methods can be used in sequence as displayed, or in combination to generate an overall confidence metric, or an array of scenarios. Results can be pushed to integrated platforms with the use of an API (2430), or other methods. Results can also be presented to users in the form of a graphical interface or reports (2432).

In order to achieve the desired method and system of food classification, usage, and waste analysis, a physical device is used. This device could be a phone or tablet for specific applications. For many applications a custom device has been built to capture the required data automatically or with manual input. This device consists of various components that complete the desired steps in the methodology and system.

One or many sensors can be used in the device to gather the relevant data, including; visual camera, stereo camera, NIR (Near-infrared) sensor and emitter, other hyperspectral sensors, laser scanners, LIDAR, radar, ultrasound sensors, optical projector, manual triggers, load cell and more. These sensors (1802, 1812, 1902, 2002, 2004) make up a large quantity of the data that determines if a food object is detected (204, 304, 402). The data from these sensors make up large amounts of the data stream (1904, 2012, 2312) that the processor (600) uses to calculate the relevant food characteristics, insights and trends.

Sensors are not necessarily related to direct food data collection. Other sensors are used to in the human machine interface (or user interface) to collect user input data. Manual inputs for events or data entry come from buttons, switches, keypad, number pad, keyboard, mouse, touchscreen, load cells, dial, knob, pressure sensor, motion sensor, hand gesture recognition, audio recognition, natural language processing, cord, or similar systems/mechanisms. Additional sensors can also be used to monitor the environment at the device location. Examples of these include humidity, temperature, pressure, air quality, air composition, smell/odor, liquid, gas, or fluid composition, or similar environmental features.

The sensor data is sent to the processor. The processor uses the sensor data in a variety of ways, including to find the region of interest (306,404), to analyze properties of the food (206), capture discreet data (e.g. image), or continuous data (e.g. video) of the region of interest (which could be the entire visible area, an area where food is present, an area where food is not present, or a targeted section of the food area) (406), determine if continuous or discreet data collection should be used (2316), determine food characteristics (e.g. mass, weight, food category/type, volume, color, composition, quality, attributes, dimensions, features, defects) (206, 308, 310, 314, 408, 1804, 1814, 1906, 2014), used in machine learning models (410, 1806, 1816, 1906, 2014), determine if an object is food or not (312, 424), determine if data should be captured and/or saved (2314), analyze features and/or defects (FIG. 16), other food related methods and processes discussed in this application, and significantly similar methods and processes. The quantity of data that is processed on the processor, or transferred to external servers (on-premises, in the cloud, or other server(s)), varies depending on the specific application.

The processor carries out other device functionality including managing all connected devices including sensors (704), restarting, cycling connections, powering, or turning off power to connected devices (704), tracking serial numbers, routing data to correct system steps (704), along with other device management functionality. The processor controls the user interface (also known as the human machine interface) if it is present (706, 804), device diagnostic data logging, saving, and sending, connections to external servers or other external devices and databases (710, 712). The processor controls the data transfer to an external server (712, 820), which could be on-premises, in the cloud, or at another location. The processor(s) perform all or the majority of computational tasks that take place on the device.

Light emitters (typically LEDs) are used in scenarios where they improve the scene, allowing for higher quality sensor data. Light emitters can be within the enclosure or installed outside the enclosure, depending on the specific application. In certain circumstances where controlling lighting is particularly important, a canopy or other obstructer can be used to block lighting from other sources. This additional apparatus is typically used in food processing applications, to reduce errors caused by differences in color, glare, blur, shadows, or other lighting features. These lighting features can cause an instant reduction in accuracy if present, but also can have an impact on data over a period of time if they are variable over time.

An ingress protection enclosure is used to ensure components that require protection from external elements are protected. Particularly the processor (600) and sensors that do not have their own ingress protection (702, 806) need protection against ingress. For locations such as kitchens and industrial food processors this ingress protection enclosure is crucial, particularly in areas that are hosed down with water during cleaning. In areas such as a cafeteria serving line, ingress protection may not be as critical, and more cost-efficient enclosures or housings can be used.

An electronics holder is designed to hold sensors and the processor in place, along with any additional inputs or outputs that can be attached to the electronics holder. This electronics holder ensures that sensors are held in the correct position, and not subject to movement in the event of a bump, vibration, perturbation, drop, fall, etc. This is critical to ensure sensors are positioned correctly for high sensor quality data collection, and to reduce damage to components if any of the previously mentioned events occur. The electronics holder is custom designed to house the sensors used for specific applications and the processor.

The positioning arm ensures the relevant sensor(s) (702, 806) are oriented correctly in three dimensional space to collect high quality sensor data. The positioning arm can be customized depending on the application, with variable length, width, thickness, enclosure/sensor mounting position, angled surfaces (to allow for specific sensor positioning, for food safety and hygiene, or other purpose), and mounting method. If a sensor, group of sensors, ingress protection enclosure, or other housing/enclosure is mounted/attached straight to a surface (e.g. wall, ceiling, roof, workstation, machinery, canopy, etc.) a positioning arm may be omitted if not necessary to orient sensors to collect high quality sensor data.

The attachment system can consist of a clamping mechanism, adhesive mechanism, fastener mechanism, or a hanging mechanism. The attachment system ensures the entire device is stable and robustly in position to ensure high quality sensor data.

A suit of user interface (also known as human machine interface) options can be equipped to devices. A "headless" device has no user interface, transferring data to be integrated into other systems, or to be displayed on an Application Interface (814) that is not part of the device. This Application Interface could be on a mobile device, smart phone, tablet, computer, dashboard display, or any other display system. A simple set of light indicators can be used for a basic user interface. Lights of different colors (typically LEDs) can be used to communicate with the user or other persons. Different patterns and timings can be used for more complex communication, e.g. for debugging, maintenance, or more detailed communication (one example being the number of green flashes relating to a quality level in a quality control scenario). Visual displays such as seven segment character displays and visual screens can be used to communicate to the user or other persons (706, 804).

The device unlocks the ability to perform improved human tasks (e.g. trimming, quality control, slicing, inspection, production, baking, or other human-led food transformative processes). The device output data can also be integrated with robotic interfaces and mechanical systems (referred to as "mechanical systems" going forward) to assist human-led food transformative processes, mechanical system led food transformative processes (with human assistance), or fully autonomous food transformative processes. Examples of mechanical systems include motor driven devices, robotic arms, end-effectors, laser cutters, laser guide projectors, and similar systems. Mechanical systems can perform basic or complex tasks with high levels of precision. Using the device outlined in this application, these mechanical systems can unlock high quality sensor data to achieve high accuracy in their food transformation tasks.

FIG. 25A and FIG. 25B shows an embodiment of the device that is being used. FIG. 25A shows the device (2502) mounted next to a scan table for the food tray to be scanned. FIG. 25B shows the orientation of the light path (2504) from the device to the table below.

What is claimed is:

1. A system to measure a food characterization, food consumption, food usage and food waste, comprising:
   a specific device to gather an image of a food object at a facility to identity of a food object, the food object before consumption and wastage of the food object after consumption, wherein the food object includes food or particular items of food;
   a computer having a user interface to manage individual data collection points for the image of the food object, data capturing for the image of the food object, data analysis of the food object;
   a service layer to connect a central processing unit hosted in a server locally or in cloud, service application programming interface (API) to connect to a proprietary application layer and to a database module for the data collection of the food object;
   a sensor module to acquire a single image or multiple images of the food object before and after its use or transformation in any manner captured by the specific device;
   an image acquisition module collects the single image from the sensor module of the specific device and stores in a database;

an image analysis module collects the data acquired from the sensor module, including the single image or multiple images of the food object, the database module and a training module to perform processing in the central processing unit of the data and the image acquired using the device sensor in the specific device and processes the data to be provided to a user, client or an analyst;

the database stores the said images received from the device sensor of the specific device, the sensor module, the specific device and the image acquisition module and provides input to an analytical module for analysis and a user interface module for visualization of a client data;

a client module registers the specific device to a specific client in the central processing unit and enables a data acquisition and analysis;

a device manager module to identify flash secure digital card (SD) in the central processing unit assigned to the specific device for collecting location, registration, initialization and launching a software application for the said specific device;

the training module to receive a data training set, convert the data training set to a model, upload the model to a training process and train the model for the food characterization, food consumption and food waste; and the analytical module uses the data training set to identify the food characterization, food consumption, food usage and calculates the food waste.

2. The system of claim 1, wherein the food characterization is differentiating between the food object and a non-food object and classifying between the food object and food waste, wherein food consumption is predicted after calculating a volumetric calculation before and after use of the food object image is acquired, wherein food usage is determined after the data collected from the device sensor of the specific device, the sensor module, the specific device and the image acquisition module to reduce food waste using data from portion sizing, preparation changes, ingredient usage, customer feedback, and supplier changes, wherein food waste is unused food after food consumption, preparation and processing of food itself, wherein the client specific data is individual client's specific data, wherein the specific device is a registered device to a device registry for every client separately.

3. A method to measure a food characterization, food consumption, usage and food waste, comprising:
placing a specific device having a sensor to capture an image of a food object;
detecting the food object contained in a food storage container using the specific device in a serving container and a disposal container;
analyzing a property for the food object, wherein the property is one of a label, mass, shape, color, composition, morphology, and volume;
aggregating a time based data for the food characterization, food consumption, usage and food waste in the specific client place for the food object;
generating of results for at least one of a food quality, food presentation, food procurement, food mass, usage trend, wastage trend while prepping, per plate food distribution, per plate food consumption, shelf life dependent wastage, consumption wastage, popular food vs unpopular food on the menu, more trendy food item, nutritional value that was consumed for personal use, seasonal inflow of perishable, wastage, and a combination thereof, by calculating using a stored and an immediate data using cloud storage and processing algorithms; and sharing the results with the specific client who has installed the device in their facility, wherein the food characterization is differentiating between the food object and a non-food object and classifying between the food object and food waste, wherein food waste is unused food after food consumption, preparation and processing of food itself.

4. The method of claim 3, further comprising:
inserting a flash secure digital card (SD) into the specific device;
registering the device on a cloud in a backend based upon a network request from the inserted flash secure digital (SD) card;
configuring a custom software for the food characterization, transformation, food consumption and food waste calculations for the specific client; and
uploading the custom software for the food characterization, food consumption and food waste calculation.

5. The method of claim 3, further comprising;
training the model set using the training module for a model prediction based on a parameter and implementing the results of a trained set for detecting the food object in a production line.

6. This method of claim 5, further comprising;
creating an annotation for the food object as a bounding box coordinates with corresponding food labels tied to the image; wherein a minimum and maximum dimension along a given length and width (xmin, ymin), (xmax, ymax) points for each food object identified in the image as the bounding box for the food object detection analysis; and
converting a polygon points to the bounding box by finding the maximum width and height of the polygon as the width and height of a resulting bounding box for the food object detection analysis.

7. The method of claim 6, further comprising;
analyzing features and defects of the food object, wherein the defects of the food object are bruises, processing error, cuts, ageing, ripening, lump, craters, by calculating the minimum and maximum dimension along a given length and width of the food object the image and converting from a pixel to meter.

8. The method of claim 3, further comprising;
analyzing the data using several data points, wherein the data points are a time, date, manual trigger, color thresholding, volumetric thresholding, load cell, machine learning model output, time of flight sensor thresholding, lidar, radar, hyperspectral thresholding including near infrared thresholding, laser gate sensor and density thresholding.

9. The method of claim 7, further comprising;
applying a machine learning process to determine the minimum and maximum dimension along the given length and width, feature and defect in the food object.

10. The method of claim 9, further comprising;
capturing the minimum and maximum dimension along the given length and width, feature, and defect of the food object by using a width, depth, thickness, angles, color breakdown, shape, volume, cross sectional planes, custom features specific to specific food object.

11. A method to measure a food characterization, food consumption, and food waste, comprising:
placing a specific device having a sensor to capture an image of a food object as a sensor data;

detecting the food object contained in a food storage container, a serving container and a waste receptacle using the specific device;

providing a specific user interface for each user, wherein each user is one of a manager, user, a quality control user with access to specific view of a real time data, data overview, data context and quality control view based on providing a specific access;

integrating a procurement data of a food object, a usage data of the food consumption and food wastage to adjust a user specific purchasing plan, wherein the food characterization is differentiating between the food object and a non-food object and classifying between the food object and food waste, wherein food waste is unused food after food consumption, preparation and processing of food itself.

12. The method of claim 11, wherein the procurement data is collected using input from one of the sensor data, machine learning model data, time, food object feature, food object feature label, weather dependency, seasonal change in local food production, and internal client data, wherein the food object feature is one of a bruise, quality, age, texture, remaining shelf life, processing errors, cuts, ageing, ripening, lumps, discoloration and crater.

13. The method of claim 12, further comprising:

performing a statistical analysis for finding various fits to identify similarities if a historical data analysis produces a fit and trends to forecast outcome and report to the user, wherein the statistical analysis is a regression analysis.

14. The method of claim 13, further comprising;

forecasting a meal count for the day, type of meal, food object procurement, and nutritional output of the meal for the user.

15. A device to capture a data for a food characterization, food consumption, and food waste, comprising:

an electronic holder designed to hold a sensor, wherein the sensor captures the data for the food characterization, food consumption, food waste, and processor;

a printed circuit board to be used as the processor; and a positioning arm for placing the device housing the sensor in relevant places to capture an image of the food object, wherein the food characterization is differentiating between the food object and a non-food object and classifying between the food object and food waste, wherein food waste is unused food after food consumption, preparation and processing of food itself.

16. The device of claim 15, further comprising;

the electronic holder has at least one of an infrared device, image capturing device, three dimensional (3D) image capturing device and a quick response (QR) code reader.

17. The device of claim 15, wherein the processor is integrated to a database, an internet based edge device, and a user interface device using an application processing interface.

18. The device of claim 15, wherein the data for the food characterization, food consumption, and food waste to detect a defect is done using one of a characteristics of bruises, processing errors, cuts, ageing, ripening, lumps and craters.

19. The device of claim 18, further comprising:

a data analysis of the data that is captured is done using an on edge device and off device analysis and hybrid analysis with computation on edge device and off device.

20. The device of claim 15, wherein the data for food waste is tracked through processes such as trimming, preparation and after food consumption.

* * * * *